US007199137B2

(12) United States Patent
Dean et al.

(10) Patent No.: US 7,199,137 B2
(45) Date of Patent: Apr. 3, 2007

(54) IMIDAZOLE DERIVATIVES AS RAF KINASE INHIBITORS

(75) Inventors: David Kenneth Dean, Harlow (GB); Andrew Kenneth Takle, Harlow (GB); David Matthew Wilson, Harlow (GB)

(73) Assignee: SmithKline Beecham plc, Brentford, Middlesex (GB)

(*) Notice: Subject to any disclaimer, the term of this patent is extended or adjusted under 35 U.S.C. 154(b) by 111 days.

(21) Appl. No.: 10/380,891

(22) PCT Filed: Sep. 19, 2001

(86) PCT No.: PCT/GB01/04195

§ 371 (c)(1),
(2), (4) Date: Mar. 20, 2003

(87) PCT Pub. No.: WO02/24680

PCT Pub. Date: Mar. 28, 2002

(65) Prior Publication Data

US 2004/0038964 A1 Feb. 26, 2004

(30) Foreign Application Priority Data

| Sep. 21, 2000 | (GB) | ................................. | 0023193.6 |
| Sep. 21, 2000 | (GB) | ................................. | 0023196.9 |
| Sep. 21, 2000 | (GB) | ................................. | 0023197.7 |
| Sep. 21, 2000 | (GB) | ................................. | 0023208.2 |

(51) Int. Cl.
*A61K 31/4439* (2006.01)
*C07D 401/04* (2006.01)

(52) U.S. Cl. ................................. 514/341; 546/274.1

(58) Field of Classification Search ............. 546/274.1; 514/341
See application file for complete search history.

(56) References Cited

U.S. PATENT DOCUMENTS

| 5,236,917 A | 8/1993 | Dunlap et al. |
| 5,514,505 A | 5/1996 | Limburg et al. |
| 5,717,100 A | 2/1998 | Selnick et al. |
| 5,859,041 A | 1/1999 | Liverton et al. |

FOREIGN PATENT DOCUMENTS

| GB | 2 306 108 | 4/1997 |
| WO | WO 95/03297 | 2/1995 |
| WO | WO96/03387 | 2/1996 |
| WO | WO96/41645 | 12/1996 |
| WO | WO97/36587 | 10/1997 |
| WO | WO97/47618 | 12/1997 |
| WO | WO97/48672 | 12/1997 |
| WO | WO98/16227 | 4/1998 |
| WO | WO98/18788 | 5/1998 |
| WO | WO99/21555 | 5/1999 |
| WO | WO99/25717 | 5/1999 |
| WO | WO00/06124 | 11/2000 |

OTHER PUBLICATIONS

Adams J.L. et al, Recent progress towards the idnetification of selective inhibitors of serine/theronine protein kinases, Current Opinion in Drug Discovery and Development 1999 2(2) 96-109.
Adams. J.L et al, Pyrimidinylimidazole Inhibitors of CSBP/p38 Demonstrating Decreased inhibition of Hepatic Cytochrome p450 Enzymes, Bioorganic & Medical Chemistry Letters 8 (1998) 3111-3116.
Antolini M et al, Analogues of 4,5-bis(3,5-Dichlorophenyl)-2-trifluoromethyl-1H-Imidazole as Potential Antibacterial Agents. Bioorganic & Medical Chemistry Letters 9 (1999) 1023-1028.
Astles P.C. et al, Acyl-CoA:Cholesterol O-Acyltransferase (ACAT) Inhibitors.2.2-(1,3-Dioxan-2-yl)-4,5-diphenyl-1H-imidazoles as Potent Inhibitors of ACAT, J.Med.Chem. 1996, 39, 1423.
Bilodeau M. T. et al, Solid-supported synthesis of Imidazoles: A Strategy for direct resin-attachment to the Imidazole Core. J. Org. Chem 1998 63. 2800-2801.
Boehm J. C. et al. 1-Substituted 4-Aryl-5-pyridinylimidazoles: A new class of cytokine suppressive drugs with low 5-Lipoxygenase and cycloxygenase inhibitory potency, J. Med Chem 1996, 39 3929-3937.
Boehm J. C. et al, New Inhibitors of p38 Kinase, Exp Opinion Ther Patents (2000) 10 (1).
Claiborne C.F. et al, An efficient sythesis of Tertasubstituted Imidazoles from N-(2-Oxo)-amides, Tetrahedron Letters 39, (1998) 8939-8942.
Cuenda A. et al, SB203580 is a specific inhibitor of a MAP Kinase homologue which is stimulated by cellular stresses and interleukin-1, FEBS Letters 364 (1995) 229-233.
Dumas J, et al, 1-Phenyl-5-pyrazolyl Ureas Potent and Selective p38 Kinase Inhibitors, Bioorganic & Medical Chemistry Letters 10 (2000) 2051-2054.
Dumas J, et al, Discovery of a new class of p38 Kinase Inhibitors, Bioorganic & Medical Chemistry Letters 10 (2000) 2047-2050.
Eberwein D, et al, In vivo activity of a Raf kinase inhibitor in human tumor xenograft models, 406 Clinical Cancer Research vol. 6 Nov. 2000 (Supplement) Poster session 17 4547.
Gallagher T.F et al, Regulation of Stressed-Induced Cytokine Production by Pyridinylimidazole: Inhibition of CSBP Kinase; Bioorganic & Medical Chemistry vol. 5 No. 1 pp. 49-64 1997.
Garcia-Echeverria C. et al, ATP Site Directed Competitive and Irreversible Inhibtiors of Protein Kinase, Med Res Reviews 2000, 20(1), 28-57.
Hall-Jackson C.A. et al, Effect of SB203580 on the activity of c-Raf *in vitro* and *in vivo* Oncogene (1999) 18, 2047-2054.
Heimbrook, D.C. et al; Identification of Potent, Selective Inhibitors of Raf Protein Kinase, Amer. Assoc for Cancer Res New Orleans, vol. 39, p. 558, Apr. 1998.

(Continued)

*Primary Examiner*—Patricia L. Morris
(74) *Attorney, Agent, or Firm*—Grace C. Hsu; Mary E. McCarthy; Charles M. Kinzig

(57) ABSTRACT

Novel compounds (I) and their use as pharmaceuticals particularly as Raf kinase inhibitors for the treatment of neurotraumatic diseases, cancer, chronic neurodegeneration, pain, migraine and cardiac hypertrophy wherein Ar is a group of formula a) or b).

19 Claims, No Drawings

OTHER PUBLICATIONS

Henry. J. R., et al, Potent inhibitors of the Map Kinase p38, Bioorganic & Medical Chemistry Letters 8 (1998) 3335-3340.

Henry. J. R., et al, p38 mitogen-activated protein kinase as a target for drug discovery, Drugs of the Future 1999, 24 (12) 1345-1354.

Lackey K et al, The Discovery of Potent cRaf1 Kinase Inhibitors, Bioorganic & Medical Chemistry Letters 10 (2000) 223-226.

Laszlo S.E, et al, Pyrroles and other heterocycles as inhibitors of p38 Kinase, Bioorganic & Medical Chemistry Letters 8 (1998) 2689-2694.

Lee J. C. et al, p 38 Mitogen-Activtated Protein Kinase Inhibitors-Mechanisms and Therapeutic Potentials, Pharmacol Ther. vol. 82. Nos. 2-3 pp. 389-397, 1999.

Lisnock, J et al: Molecular Basis for p38 Protein Kinase Inhibitor Specificity, BioChemistry, 1998, 37, 16573-16581.

Liverton, N.J et al: Design and Synthesis of Potent, Selective and Orally Bioavailable tetrasubstituted Imidazoles of p38 Mitogen Activated Protein Kinase, J. Med Chem 1999 42 2180-2190.

Lowinger, T.B. et al, Discovery of a novel class of potent BRaf kinase inhibitors: Strucutre activity relationships 335 Clinical Cancer Research vol. 6 Nov. 2000 (Supplement) Poster session 13 4533.

P38 Inhibitors based on pyridylurea and pyridylacetoamide templates, Exp Opin. Ther. Patents (2000) 10 (7) 1151-1154.

Revesz L, et al, SAR of 4-Hydroxypiperidine and Hydroxyalkyl Substituted Heterocycles as Novel p38 Map Kinase Inhibitors, Bioorganic & Medical Chemistry Letters 10 (2000) 1261-1264.

Salituro F.G, et al, Inhibitors of p38 MAP Kinase: Therapeutic Intervention in Cytokine-Mediated Disease, Current Medicinal Chemistry 1999, 6, 807-823.

Stover D.R et al, Recent Advances in protein Kinase inhibition:Current molecular scaffolds used for inhibitor synthesis. Current Opinion in Drug Discovery and Development 1999 2(4) 274-285.

Toledo L.M. et al, The Structure-Based Design of ATP-site Directed Protein Kinase Inhibitors, Current Medicinal Chemistry 1999, 6, 775-805.

Tong L. et al, A highly specific inhibitor of human p38 MAP Kinase binds in he ATP pocket, Nature Structural Biology vol. 4 No. 4 Apr. 1997 p. 311.

Two Novel structural classes of p38 Kinase inhibitors, Exp Opin. Ther. Patents (1999) 9 (4) 477-480.

Wang Z et al, Structural basis of inhibitor selectivity in MAP Kinases, Stucture Sep. 15, 1998, 6: 1117-1128.

Young P. R. et al, Pyridinyl Imidazole Inhibitors of p38 Mitogen-activated Protein Kinase bind in the ATP site, The Journal of Biological Chemistry vol. 272 No. 18 Issue of May 2 pp. 12116-12121 1997.

IMIDAZOLE DERIVATIVES AS RAF KINASE INHIBITORS

This invention relates to novel compounds and their use as pharmaceuticals particularly as Raf kinase inhibitors for the treatment of neurotraumatic diseases, cancer, chronic neurodegeneration, pain, migraine and cardiac hypertrophy.

Raf protein kinases are key components of signal transduction pathways by which specific extracellular stimuli elicit precise cellular responses in mammalian cells. Activated cell surface receptors activate ras/rap proteins at the inner aspect of the plasma-membrane which in turn recruit and activate Raf proteins. Activated Raf proteins phosphorylate and activate the intracellular protein kinases MEK1 and MEK2. In turn, activated MEKs catalyse phosphorylation and activation of p42/p44 mitogen-activated protein kinase (MAPK). A variety of cytoplasmic and nuclear substrates of activated MAPK are known which directly or indirectly contribute to the cellular response to environmental change. Three distinct genes have been identified in mammals that encode Raf proteins; A-Raf, B-Raf and C-Raf (also known as Raf-1) and isoformic variants that result from differential splicing of mRNA are known.

Inhibitors of Raf kinases have been suggested for use in disruption of tumor cell growth and hence in the treatment of cancers, e.g. histiocytic lymphoma, lung adenocarcinoma, small cell lung cancer and pancreatic and breast carcinoma; also in the treatment and/or prophylaxis of disorders associated with neuronal degeneration resulting from ischemic events, including cerebral ischemia after cardiac arrest, stroke and multi-infarct dementia and also after cerebral ischemic events such as those resulting from head injury, surgery and/or during childbirth; also in chronic neurodegeneration such as Alzheimer's disease and Parkinson's disease; also in the treatment of pain, migraine and cardiac hypertrophy.

We have now found a group of novel compounds that are inhibitors of Raf kinases, in particular inhibitors of B-Raf kinase.

According to the invention there is provided a compound of formula (I):

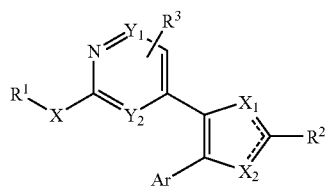

(I)

wherein

X is O, $CH_2$, CO, S or NH, or the moiety X—$R^1$ is hydrogen;

$Y_1$ and $Y_2$ are independently N or CH;

$R^1$ is hydrogen, $C_{1-6}$alkyl, $C_{3-7}$cycloalkyl, aryl, aryl$C_{1-6}$alkyl, heterocyclyl, heterocyclyl$C_{1-6}$alkyl, heteroaryl, or heteroaryl$C_{1-6}$alkyl, any of which may be optionally substituted; in addition when X is $CH_2$ then $R^1$ may be hydroxy or $C_{1-6}$alkoxy which may be optionally substituted;

$R^2$ is H, $C_{1-6}$allyl, $C_{2-6}$alkenyl, $C_{3-7}$cycloalkyl, $C_{5-7}$cycloalkenyl, heterocyclyl, aryl or heteroaryl, any of which may be optionally substituted;

Ar is a group of the formula a) or b):

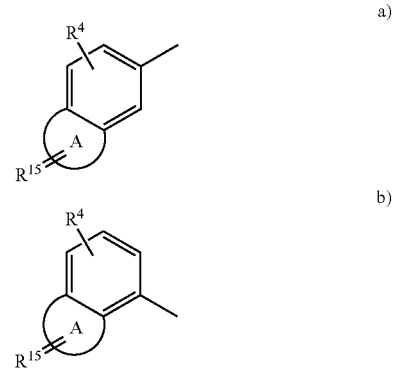

wherein A represents a fused 5- to 7-membered ring optionally containing up to two heteroatoms selected from O, S and $NR^5$, wherein $R^5$ is hydrogen or $C_{1-6}$alkyl, which ring is optionally substituted by up to 2 substituents selected from halogen, $C_{1-6}$alkyl, hydroxy, $C_{1-6}$alkoxy or keto;

$R^3$ and $R^4$ are independently selected from hydrogen, halogen, $C_{1-6}$alkyl, aryl, aryl Ci-alkyl, $C_{1-6}$alkoxy, $C_{1-6}$alkoxy$C_{1-6}$alkyl, halo$C_{1-6}$alkyl, aryl$C_{1-6}$alkoxy, hydroxy, nitro, cyano, azido, amino, mono- and di-N-$C_{1-6}$alkylamino, acylamino, arylcarbonylamino, acyloxy, carboxy, carboxy salts, carboxy esters, carbamoyl, mono- and di-N-$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkylsulphinyl or $C_{1-6}$alkylsulphonyl;

$R^{15}$ is O or N—OH;

one of $X_1$ and $X_2$ is N and the other is $NR^6$ wherein $R^6$ is hydrogen or $C_{1-6}$alkyl;

or a pharmaceutically acceptable salt thereof.

As used herein, the double bond indicated by the dotted lines of formula (I), represent the possible tautomeric ring forms of the compounds falling within the scope of this invention. It will be understood that the double bond is to the unsubstituted nitrogen.

The oxime moiety can be positioned on any of carbon atoms of the non-aromatic ring in groups a) and b).

Alkyl and alkenyl groups referred to herein, individually or as part of larger groups e.g. alkoxy, may be straight or branched groups containing up to six carbon atoms.

Cycloalkyl and cycloalkenyl groups referred to herein include groups having from three to seven and five to seven ring carbon atoms respectively.

Optional substituents for alkyl, alkenyl, cycloalkyl and cycloalkenyl groups include aryl, heteroaryl, heterocyclyl, $C_{1-6}$alkoxy, $C_{1-6}$alkylthio, aryl$C_{1-6}$alkoxy, aryl $C_{1-6}$alkylthio, amino, mono- or di-$C_{1-6}$alkylamino, aminosulphonyl, cycloalkyl, cycloalkenyl, carboxy and esters thereof, amide, ureido, guanidino, $C_{1-6}$alkylguanidino, amidino, $C_{1-6}$alkylamidino, $C_{1-6}$acyloxy, hydroxy, and halogen or any combinations thereof. A further substituent can be cyano.

Preferably the optional substituent contains a water-solubilising group; suitable solubilising moieties will be apparent to those skilled in the art and include hydroxy and amino group. Even more preferably the optional substituent includes amino, mono or di-$C_{1-6}$alkyl, amino, amino containing heterocyclyl or hydroxy or any combination thereof.

When used herein, the term "aryl" means single and fused rings suitably containing from 4 to 7, preferably 5 or 6, ring atoms in each ring, which rings, may each be unsubstituted or substituted by, for example, up to three substituents. A fused ring system may include aliphatic rings and need include only one aromatic ring. Suitable aryl groups include phenyl and naphthyl such as 1-naphthyl or 2-naphthyl.

When used herein the term "heterocyclyl" suitably includes, unless otherwise defined, non-aromatic, saturated or unsaturated, single and fused, rings suitably containing up to four heteroatoms in either or both rings, each of which is selected from O, N and S, which rings, may be unsubstituted or substituted by, for example, up to three substituents. Each heterocyclic ring suitably has from 4 to 7, preferably 5 or 6, ring atoms. A fused heterocyclic ring system may include carbocyclic rings and need include only one heterocyclic ring. Examples of heterocyclyl groups include pyrrolidine, piperidine, piperazine, morpholine, thiomorpholine, imidazolidine and pyrazolidine. Prefered examples of heterocyclyl groups include pyrrolidine, piperidine, piperazine, morpholine, imidazolidine and pyrazolidine.

When used herein, the term "heteroaryl" suitably includes, unless otherwise defined, mono- and bicyclic heteroaromatic ring systems comprising up to four, preferably 1 or 2, heteroatoms each selected from O, N and S. Each ring may have from 4 to 7, preferably 5 or 6, ring atoms. A bicyclic heteroaromatic ring system may include a carbocyclic ring. Examples of heteroaryl groups include pyrrole, quinoline, isoquinoline, pyridine, pyrimidine, oxazole, thiazole, thiadiazole, triazole, imidazole and benzimidazole.

Suitably aryl, heterocyclyl and heteroaryl groups may be optionally substituted by preferably up to three substituents. Suitable substituents include halogen, hydroxy, $C_{1-6}$alkyl, aryl, aryl$C_{1-6}$alkyl, $C_{1-6}$alkoxy, $C_{1-6}$alkoxy$C_{1-6}$alkyl, halo$C_{1-6}$alkyl, aryl$C_{1-6}$alkoxy, nitro, cyano, azido, amino, mono- and di-N-$C_{1-6}$alkylamino, acylamino, arylcarbonylamino, acyloxy, carboxy, carboxy salts, carboxy esters, carbamoyl, mono- and di-N-$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, urea, carbamate, acyl, sulphonylamino, aminosulphonyl, $C_{1-6}$alkylthio, $C_{1-6}$ alkylsulphinyl, $C_{1-6}$alkylsulphonyl, heterocyclyl, heteroaryl, heterocyclyl$C_{1-6}$alkyl and heteroaryl $C_{1-6}$alkyl, or any combination thereof. In addition two ring carbon atoms may be linked to form a bicyclic system.

When used herein halogen means fluoro, chloro, bromo or iodo.

In the compounds of formula (I):

X is preferably O, $CH_2$, S or NH, or the moiety X—$R^1$ is hydrogen.

More preferably X is $CH_2$ or NH or X—$R^1$ is hydrogen, most preferably X is NH or X—$R^1$ is hydrogen.

Preferably $Y_1$ is CH and $Y_2$ is N or CH.

Preferably $R^{15}$ is N—OH.

Alternatively, $R^1$ is hydrogen, $C_{1-6}$alkyl, aryl, aryl$C_{1-6}$alkyl, heterocyclyl, heterocyclyl$C_{1-6}$alkyl, heteroaryl, or heteroaryl$C_{1-6}$alkyl, any of which may be optionally substituted; in addition when X is $CH_2$ then $R^1$ may be hydroxy or $C_{1-6}$alkoxy which may be optionally substituted.

$R^2$ can be $C_{1-6}$alkyl, $C_{2-6}$alkenyl, $C_{3-7}$cycloalkyl, $C_{5-7}$cycloalkenyl or heterocyclyl, any of which may be optionally substituted. Alternatively $R^2$ is aryl or heteroaryl, either of which may be optionally substituted.

Preferably Ar is a group Ar is a group of the formula a) or b):

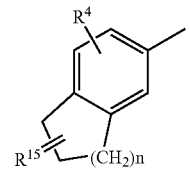

a)

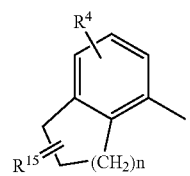

b)

$R^4$ is as defined for compounds of formula (I), n is 1, 2 or 3 and $R^{15}$ is O or N—OH.

More preferably Ar is a group of formula a) or b)

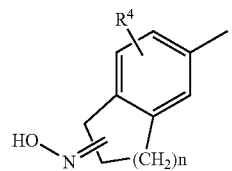

a)

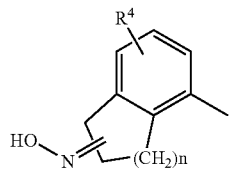

b)

wherein $R^4$ is as defined for compounds of formula (I), and n is 1, 2 or 3.

n is preferably 1.

Ar is preferably an indone group

Suitable optional substituents for the group $R^2$ include one or more groups selected from the group consisting of aryl, heteroaryl, heterocyclyl, $C_{1-6}$alkoxy, $C_{1-6}$alkylthio, aryl$C_{1-6}$ alkoxy, aryl$C_{1-6}$alkylthio, amino, mono- or di-$C_{1-6}$alkylamino, aminosulphonyl, cycloalkyl, cycloalkenyl, carboxy and esters thereof, amide, ureido, guanidino, $C_{1-6}$alkylguanidino, amidino, $C_{1-6}$alkylamidino, $C_{1-6}$acyloxy, hydroxy, and halogen or any combinations thereof. Alternatively the substituent can be $C_{1-6}$alkylaryl $R^2$ is preferably a group that contains a solubilising moiety, suitable solubilising moieties will be apparent to those skilled in the art and include basic groups. Particular solubilising groups that can be mentioned include amine and hydroxy groups. For example, amino, mono-or di-$C_{1-6}$alkylamino, amine containing heterocyclyl or hydroxy groups or any combination thereof.

Specific $R^2$ groups that may be mentioned include —$CR^7R^8$—$CH_2$-Z, —$CH_2$-Z and heterocyclyl, wherein $R^7$ and $R^8$ independently represent optionally substituted $C_{1-6}$alkyl, or $R^7$ and $R^8$ together with the carbon atom to which they are attached form an optionally substituted $C_{3-7}$cycloalkyl or $C_{5-7}$cycloalkenyl ring; and Z is $NR^9R^{10}$, $NR^9C(O)NR^9R^{10}$, $NR^9COOR^{10}$, $NR^9SO_2R^{10}$, $NR^9C(Q)R^{10}$ or heterocyclyl wherein $R^9$ and $R^{10}$ are independently selected from hydrogen, $C_{1-6}$alkyl, $C_{3-7}$cycloalkyl, heterocyclyl, heterocyclyl$C_{1-6}$alkyl, aryl, aryl$C_{1-6}$alkyl, heteroaryl and heteroaryl$C_{1-6}$alkyl, any of which may be optionally substituted or together form a heterocyclic group, when present as $NR^9R^{10}$; Q is O or S, preferably O; and when $R^2$ or Z is heterocyclyl, e.g. piperidyl, piperazine or morpholine, the heterocyclyl group is optionally substituted.

Specific $R^2$ groups that may be mentioned include optionally substituted phenyl, pyridyl, pyrimidyl and furanyl.

Further specific $R^2$ groups which may be mentioned included phenyl substituted by a group $-O-(CH^2)_m-NR^{18}R^{19}$ or $-(CH_2)_m-NR^{18}R^{19}$, wherein m is an integer from 1 to 6, e.g. 2 or 3, and $R^{18}$ and $R^{19}$ independently represent hydrogen, $C_{1-6}$alkyl, or $R^{18}$ and $R^{19}$ together with the nitrogen atom to which they are attached form an optionally substituted 5- to 7-membered ring optionally containing an additional heteroatom selected from $NR^{20}$ and O, wherein $R^{20}$ is hydrogen or $C_{1-6}$alkyl, e.g. morpholinyl.

Alternatively $R^7$ or $R^8$ can be hydrogen.

$R^3$ is preferably hydrogen.

$R^4$ is preferably hydrogen.

$R^6$ is preferably hydrogen.

The compounds of formula (I) preferably have a molecular weight of less than 800.

It will be understood that the invention includes pharmaceutically acceptable derivatives of compounds of formula (I) and that these are included within the scope of the invention.

Particular compounds according to the invention include those mentioned in the examples and their pharmaceutically acceptable salts. As used herein "pharmaceutically acceptable derivatives" includes any pharmaceutically acceptable salt, ester or salt of such ester of a compound of formula (I) which, upon administration to the recipient, is capable of providing (directly or indirectly) a compound of formula (I) or an active metabolite or residue thereof.

Preferably the derivative is a salt

Particular compounds according to the invention include those mentioned in the examples and their pharmaceutically acceptable salts.

It will be appreciated that for use in medicine the salts of the compounds of formula (I) should be pharmaceutically acceptable. Suitable pharmaceutically acceptable salts will be apparent to those skilled in the art and include those described in *J. Pharm. Sci.*, 1977, 66, 1–19, such as acid addition salts formed with inorganic acids e.g. hydrochloric, hydrobromic, sulphuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention.

The compounds of this invention may be in crystalline or non-crystalline form, and, if crystalline, may optionally be hydrated or solvated. This invention includes within its scope stoichiometric hydrates as well as compounds containing variable amounts of water.

The invention extends to all isomeric forms including stereoisomers and geometric isomers of the compounds of formula (I) including enantiomers and mixtures thereof e.g. racemates. The different isomeric forms may be separated or resolved one from the other by conventional methods, or any given isomer may be obtained by conventional synthetic methods or by stereospecific or asymmetric syntheses.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Compounds of formula (I) are imidazole derivatives which may be readily prepared using procedures well-known to those skilled in the art, and described in, for instance, Comprehensive Heterocyclic Chemistry, Editors Katritzky and Rees, Pergamon Press, 1984, 5, 457–497, from starting materials which are either commercially available or can be prepared from such by analogy with well-known processes.

Examples of processes for preparing compounds of this invention are as outlined in schemes 1 and 2. The schemes illustrate the production of compounds in which $-X-R^1$, $R^3$ and $R^4$ are hydrogen, $X_1$ is NH, $Y_1$ and $Y_2$ are CH and Ar is a group of formula a) wherein n is 1, however the processes are applicable for the production of all the compounds of formula (I). In the first such process (scheme 1), α-diketones are prepared by reaction of the anion of an O-protected derivative of 4-pyridine-methanol, with a suitably protected fused bicyclic aryl-aldehyde wherein PG is an oxime protecting group e.g. $=N-OR^{11}$ wherein $R^{11}$ is optionally substituted $C_{1-6}$alkyl, e.g. methyl, optionally substituted aryl or silyl, or PG is a ketone protecting group. O-deprotection followed by oxidation of the intermediate diol affords the aforementioned α-diketones. Reacting the diketone with a suitable aldehyde and ammonium acetate in a solvent e.g. acetic acid, methoxy$^t$butylether, or methanol, allows access to the imidazole nucleus. Thereafter, the group $R^2$ may be converted into another group $R^2$, using conventional functional group interconversion procedures, and the group PG converted into an oximino group ($=N-OH$).

Scheme 1

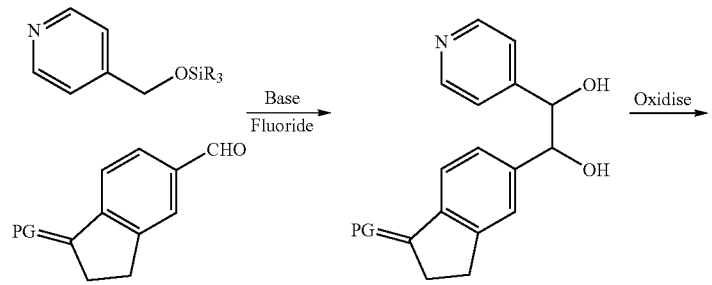

-continued

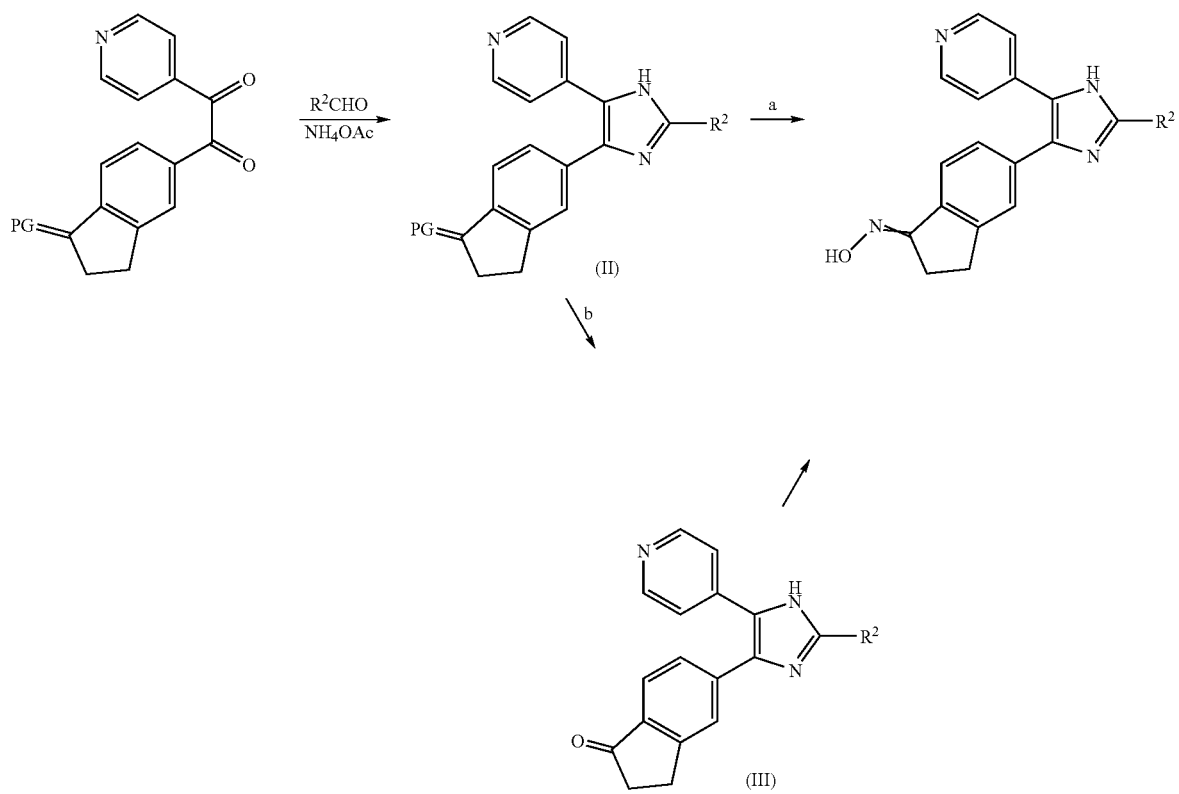

The second such process (scheme 2) is analogous to that described by Liverton et al (J. Med. Chem., 1999, 42, 2180). In this approach, 2-bromo-1-pyridine-4-yl-ethanone is reacted with a suitable amidine to form the central imidazole nucleus. Protection of the labile imidazole hydrogen (typical protecting groups, PG', are 2-trimethylsilyl-ethoxymethyl-, SEM, and methoxymethyl-, MOM) then allows metallation of the imidazole ring. Introduction of the remaining substituent can then be achieved by a transition metal catalysed cross-coupling of the metallated imidazole with a suitably protected, fused bicyclic aromatic system substituted with a halogen or sulphonate ester, wherein PG is =O or a protecting group as defined for Scheme 1 above. Such transition metal coupling procedures are well known to those skilled in the art and described in, for instance, D. W. Knight in Comprehensive Organic Synthesis, volume 4, page 481, editors B. M. Trost and I. Fleming, Pergamon Press, 1991. Thereafter, the group $R^2$ may be converted into another group $R^2$, using conventional functional group interconversion procedures, the protecting group PG' removed and the group PG converted into an oximino group (=N—OH). It will also be appreciated that the cross-coupling procedure could be reversed such that a halogenated imidazole is coupled with a suitably protected, metallated fused bicyclic aromatic system Scheme 2

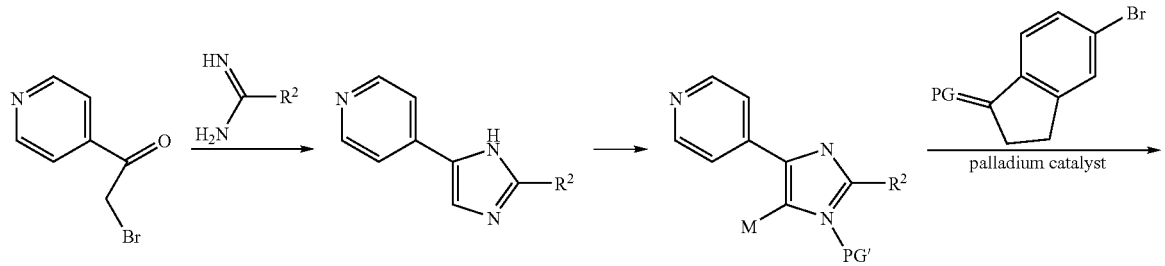

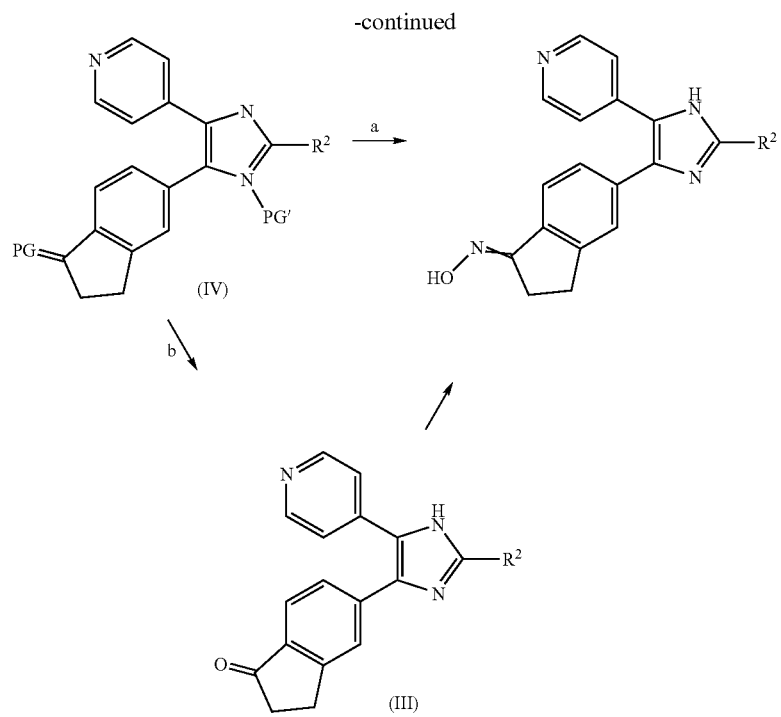

Compounds of formula (I) wherein $R^6$ is $C_{1-6}$ alkyl may be produced by alkylation of a compound of formula (II), following removal of the protecting group PG', by a process analogous to that described by Liverton et al (J. Med. Chem., 1999, 42, 2180). The resulting isomers may be separated by chromatographic techniques.

During the synthesis of the compounds of formula (I) labile functional groups in the intermediate compounds, e.g. hydroxy, carboxy and amino groups, may be protected. A comprehensive discussion of the ways in which various labile functional groups may be protected and methods for cleaving the resulting protected derivatives is given in for example *Protective Groups in Organic Chemistry*, T. W. Greene and P. G. M. Wuts, (Wiley-Interscience, New York, 2nd edition, 1991).

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable salts thereof.

Pharmaceutically acceptable salts may be prepared conventionally by reaction with the appropriate acid or acid derivative.

Various of the intermediates used in the production of the compounds of formula (I) are novel thus according to a further aspect of the invention there is provided a compound of formula (II), (III) or (IV), wherein PG represents =O or a protecting group and PG' represents a protecting group. Suitable protecting groups include those described above.

As indicated above the compounds of formula (I) and their pharmaceutically acceptable derivatives are useful for the treatment and/or prophylaxis of disorders in which Raf kinases, in particular B-Raf kinase, are implicated.

According to a further aspect of the invention there is provided the use of a compound of formula (I) or a pharmaceutically acceptable derivatives thereof as an inhibitor of B-Raf kinase.

As indicated above the compounds of formula (I) and their pharmaceutically acceptable derivatives are useful for the treatment and/or prophylaxis of disorders associated with neuronal degeneration resulting from ischemic events, as well as chronic neurodegeneration, pain, migraine and cardiac hypertrophy.

According to a further aspect of the invention there is provided a method of treatment or prophylaxis of a neurotraumatic disease, in a mammal in need thereof, which comprises administering to said mammal an effective amount of a compound of formula (I) or a pharmaceutically acceptable derivative thereof.

According to a further aspect of the invention there is provided the use of a compound of formula (I) or a pharmaceutically acceptable derivative thereof in the manufacture of a medicament for the prophylactic or therapeutic treatment of any disease state in a human, or other mammal, which is exacerbated or caused by a neurotraumatic event.

Neurotraumatic diseases/events as defined herein include both open or penetrating head trauma, such as caused by surgery, or a closed head trauma injury, such as caused by an injury to the head region, Also included within this definition is ischemic stroke, particularly to the brain area, transient ischemic attacks following coronary by-pass and cognitive decline following other transient ischemic conditions.

Ischemic stroke may be defined as a focal neurologic disorder that results from insufficient blood supply to a particular brain area, usually as a consequence of an embolus, thrombi, or local atheromatous closure of the blood vessel. Roles for stress stimuli (such as anoxia), redox injury, excessive neuronal excitatory stimulation and inflammatory cytokines in this area has been emerging and the present invention provides a means for the potential treatment of these injuries. Relatively little treatment, for an acute injury such as these has been available.

The compounds of the invention may also be used in the treatment or prophylaxis of cancers.

According to a further aspect of the invention there is provided a method of treatment or prophylaxis of a cancer, in a mammal in need thereof, which comprises administering to said mammal an effective amount of a compound of formula (I) or a pharmaceutically acceptable derivative thereof.

According to a further aspect of the invention there is provided the use of a compound of formula (I) or a pharmaceutically acceptable derivative thereof in the manufacture of a medicament for the prophylactic or therapeutic treatment of cancer.

According to a further aspect of the invention there is provided a method of treatment or prophylaxis of a chronic neurogeneration, pain, migraine and cardiac hypertrophy, in a mammal in need thereof, which comprises administering to said mammal an effective amount of a compound of formula (I) or a pharmaceutically acceptable derivative thereof.

According to a further aspect of the invention there is provided the use of a compound of formula (I) or a pharmaceutically acceptable derivative thereof in the manufacture of a medicament for the prophylactic or therapeutic treatment of chronic neurogeneration, pain, migraine and cardiac hypertrophy.

In order to use the compounds of formula (I) in therapy, they will normally be formulated into a pharmaceutical composition in accordance with standard pharmaceutical practice.

According to a further aspect of the invention there is provided a pharmaceutical composition comprising a compound of formula (I) or a pharmaceutically acceptable derivative thereof and a pharmaceutically acceptable carrier.

The compounds of formula (I) may conveniently be administered by any of the routes conventionally used for drug administration, for instance, parenterally, orally, topically or by inhalation. The compounds of formula (I) may be administered in conventional dosage forms prepared by combining it with standard pharmaceutical carriers according to conventional procedures. The compounds of formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier is dictated by the amount of compound of formula (I) with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. When a liquid carrier is used, the preparation will be in the form of a syrup, emulsion, soft gelatin capsule, sterile injectable liquid such as an ampoule or nonaqueous liquid suspension.

The compounds of formula (I) are preferably administered parenterally, that is by intravenous, intramuscular, subcutaneous, sublinqual, intranasal, intrarectal, intravaginal or intraperitoneal administration. The intravenous form of parenteral administration is generally preferred. The compounds may be administered as a bolus or continuous infusion e.g. for 6 hours up to 3 days. Appropriate dosage forms for such administration may be prepared by conventional techniques.

The compounds of formula (I) may also be administered orally. Appropriate dosage forms for such administration may be prepared by conventional techniques.

The compounds of formula (I) may also be administered by inhalation, that is by intranasal and oral inhalation administration. Appropriate dosage forms for such administration, such as aerosol formulations, may be prepared by conventional techniques.

The compounds of formula (I) may also be administered topically, that is by non-systemic administration. This includes the application of the inhibitors externally to the epidermis or the buccal cavity and the instillation of such a compound into the ear, eye and nose, such that the compound does not significantly enter the blood stream.

For all methods of use disclosed herein the daily oral dosage regimen will preferably be from about 0.1 to about 200 mg/kg of total body weight, preferably from about 0.2 to 30 mg/kg, more preferably from about 0.5 to 15 mg/kg. The daily parenteral dosage regimen about 0.1 to about 200 mg/kg of total body weight, preferably from about 0.2 to about 30 mg/kg, and more preferably from about 0.5 to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of the inhibitors will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of the inhibitors given per day for a defined number of days, can be ascertained by those skilled in the art using conventional course of treatment determination tests. In the case of pharmaceutically acceptable salts the above figures are calculated as the parent compound of formula (I).

No toxicological effects are indicated/expected when a compound of formula (I) is administered in the above mentioned dosage range.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention.

The abbreviations used herein are as follows:
THF means tetrahydrofuran
DMF means N,N-Dimethylforamide
TBAF means tetrabutylammonium fluoride
DMSO means dimethylsulfoxide
LDA means lithium diisopropyl amide

EXAMPLE 1

5-[2-(2-Amino-1,1-dimethyl-ethyl)-5-pyridin-4-yl-1H-imidazol-4-yl]-indan-1-one oxime

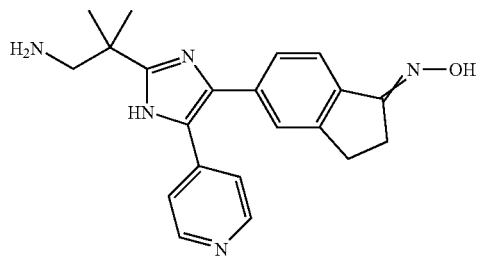

Step 1: 5-Bromo-indan-1-one O-methyl-oxime

To a solution of 5-bromo-indanone (100 g, 0.474 mol) in ethanol (650 ml) under argon was added methoxylamine hydrochloride (198 g, 2.38 mol) and pyridine (125 ml). The mixture was refluxed for 2.5 hours, cooled to room temperature and poured into saturated aqueous sodium hydrogen carbonate solution. The mixture was then extracted with ethyl acetate and the organic phase dried (Na$_2$SO$_4$) and then concentrated in vacuo. The crude material was recrystallised from isopropanol to furnish the title compound, (110 g, 97%), as a brown solid; $^1$H NMR (CDCl$_3$) 7.52 (1H, d, J 8.3 Hz), 7.43 (1H, d, J 1 Hz), 7.35 (1H, dd, J 8.3, 1 Hz), 3.97 (3H, s), 2.99 (2H, m), 2.99 (2H, m), 2.85 (2H, m).

Step 2: 1-Methoxyimino-indan-5-carbaldehyde

To a solution of the product of Step 1 (112 g, 0.46 mol) in THF (1500 ml) at −60° C. under argon, was added n-BuLi (325 ml, 0.52 mol) over 1 hour. After stirring at −60° C. for 1 hour a solution of DMF (39.7 ml) in THF (50 ml) was added dropwise over 1 hour. The reaction was stirred at −60° C. for 1 hour before being allowed to warm to room temperature. After 1 hour the reaction was quenched with saturated aqueous sodium hydrogen carbonate solution and extracted into ethyl acetate. The organic phase was then dried (Na$_2$SO$_4$), concentrated in vacuo and the residue purified by silica gel chromatography, to give the title compound (57 g, 65%) as a yellow solid; $^1$H NMR (CDCl$_3$) 10.0 (1H, s), 7.83–7.73 (3H, m), 4.02 (3H, s), 3.10 (2H, m), 2.92 (2H, m).

Step 3: 5-(1,2-Dihydroxy-2-pyridin-4-yl-ethyl)-indan-1-one-O-methyl-oxime

To a solution of 4-(tert-butyl-dimethyl-silanyloxymethyl)-pyridine [T. F. Gallagher et al, Bioorg. Med. Chem., 1997, 5, 49] (71.5 g, 0.32 mol) in THF (800 ml) at −50° C. under argon was added LDA (162 ml, 2M in heptane/THF/ethylbenzene, 0.324 mol) over 1 hour. The mixture was stirred at −40° C. for a further 1 hour before a solution of the product of Step 2 (55 g, 0.29 mol) in THF (600 ml) was added over 1 hour. The reaction was then allowed to warm to room temperature overnight before being quenched by the addition of saturated aqueous sodium hydrogen carbonate solution and then extracted into ethyl acetate. The organic phase was dried (Na$_2$SO$_4$) and concentrated in vacuo to give a brown oil (125 g).

The oil was then dissolved in THF (1500 ml), treated with TBAF (356 ml, 0.356 mol) and stirred for 1 hour. The reaction mixture was then evaporated and the residue partitioned between water and ethyl acetate. The organic phase was then dried (Na$_2$SO$_4$) and concentrated to give the title compound (57 g, 64%) as a pale yellow solid which was used without further purification. $^1$H NMR (CDCl$_3$) 8.38 (2H, m), 7.57 (1H, m), 7.12–6.99 (4H, m), 4.88 (1H, m), 4.66 (1H, m), 3.96 (3H, s), 2.93 (2H, m), 2.85 (2H, m).

Step 4: 1-(1-Methoxyimino-indan-5-yl)-2-pyridin-4-yl-ethane-1,2-dione

To a mixture of DMSO (43 ml, 0.56 mol) and dichloromethane (800 ml) at −70° C. under argon, was added oxalyl chloride (71.4 g) and then a solution of the product of Step 3 (55 g, 0.185 mol) in a mixture of dichloromethane/DMSO (1000 ml/60 ml) over 2 hours at −60° C. After stirring for 2 hours at −60° C., triethylamine (154 ml) was added dropwise and the mixture then allowed to warm to room temperature overnight. The reaction mixture was then quenched with water, the organic phase separated then washed with water, dried (Na$_2$SO$_4$) and concentrated to yield the title compound (51 g, 94%) as a yellow solid. $^1$H NMR (CDCl$_3$) 8.87 (2H, d), 7.89–7.77 (5H, m), 4.03 (3H, s), 3.09 (2H, m), 2.93 (2H, m).

Step 5: {2-[4-(1-Methoxyimio-indan-5-yl]-5-pyridin-4-yl-1H-imidazol-2-yl]-2-methyl-propyl}-carbamic acid tert-butyl ester A mixture of the product of Step 4 (1.02 g, 3.47 mmol), (2,2-dimethyl-3-oxo-propyl)-carbamic acid tert-butyl ester (0.84 g, 4.16 mmol) [Y. Guindon et al, J. Am. Chem. Soc., 1997, 119, 9289] and ammonium acetate (1.34 g, 17.4 mmol) in MeOH (15 ml) and tert-butyl methyl ether (30 ml) was stirred at room temperature for 2 hours. The reaction was then poured into water and extracted with ethyl acetate. The organic extract was then dried (MgSO$_4$), concentrated in vacuo and the crude material purified by silica gel chromatography eluting with ethyl acetate to give the title compound (0.450 g, 27%) as a colourless solid; MS(AP+) m/e 477 [M+H]$^+$ Step 6: 5-[2-(2-Amino-1,1-dimethyl-ethyl)-5-pyridin-4-yl-1H-imidazol-4-yl]-indan-1-one A mixture of the product of Step 5 (0.400 g, 0.839 mmol) and 5M HCl (2 ml) in dioxan (4 ml) was heated to 100° C. for 1 hour. Acetone (10 drops) was then added and the heating continued for a further 1 hour before the mixture was cooled to room temperature and reduced in vacuo. The residue was purified by silica gel chromatography, eluting with a 2:18:80 mixture of 0.88 ammonia solution:methanol:ethyl acetate to give the title compound (0.18 g, 62%) as a yellow solid; MS(AP+) m/e 348 [M+H]$^+$.

Step 7: 5-[2-(2-Amino-1,1-dimethyl-ethyl)-5-pyridin-4-yl-1H-imidazol-4-yl]-indan-1-one oxime To a solution of the product of Step 6 (0.12 g, 0.350 mmol) in ethanol (5 ml) at 80° C. was added aqueous hydroxylamine (0.07 g, 1.04 mmol, 50% in water). After 30 min the mixture was cooled to room temperature and concentrated in vacuo to give the title compound, (0.124 g, 100%) as a yellow solid; MS(AP+) m/e 362 [M+H]$^+$.

EXAMPLE 2

N-{2-[5-(1-Hydroxyimino-indan-5-yl)-4-pyridin-4-yl-1H-imidazol-2-yl]-2-methyl-propyl}-methane-sulfonamide

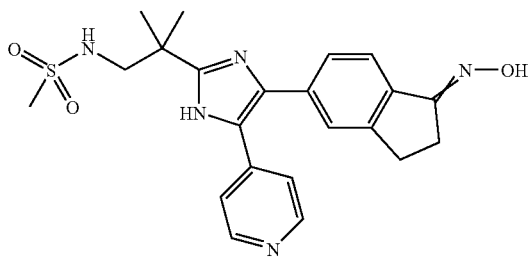

Step 1: N-{2-Methyl-2-[5-(1-oxo-indan-5-yl)-4-pyridin-4-yl-1H-imidazol-2-yl]-propyl}-methanesulfonamide A mixture of the product of Example 1, Step 6 (0.1 g, 0.29 mmol) and methane sulphonyl chloride (0.023 ml, 0.3 mmol) in dichloromethane (3 ml) was stirred at room temperature for 2 hours. The reaction was then poured into ethyl acetate, washed with water and aqueous sodium hydrogen carbonate solution, dried (MgSO$_4$) and concentrated in vacuo. The crude residue was then purified by silica gel chromatography eluting with a 1:9:90 mixture of 0.88 ammonia solution:methanol:dichloromethane to give the title compound (0.075 g, 61%) as a yellow solid; MS(AP+) m/e 425 [M+H]$^+$.

Step 2: N-{2-[5-(1-Hydroxyimino-indan-5-yl)4-pyridin-4-yl-1H-imidazol-2-yl]-2-methyl-propyl}-methanesulfonamide The title compound (0.06 g, 90%) was prepared from the product of Step 1 as described in Example 1 Step 7; MS(AP+) m/e 440[M+H]$^+$.

EXAMPLE 3

1-(2-Methoxy-ethyl)-piperidine-4-carboxylic acid {2-[5-(1-hydroxyimino-indan-5-yl)-4-pyridin-4-yl-1H-imidazol-2-yl]-2-methyl-propyl}-amide

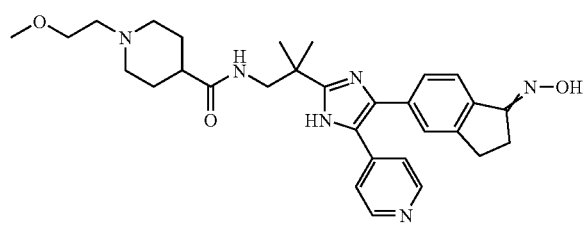

Step 1:1 -(2-Methoxy-ethyl)-piperidine-4-carboxylic acid {2-methyl-2-[5-(1-oxo-indan-5-yl)-4-pyridin-4-yl-1H-imidazol-2-yl]-propyl}-amide A mixture of the product of Example 1, Step 6 (0.1 g, 0.29 mmol), 1-hydroxybenzotriazole (0.06 g, 0.44 mmol) and polymer bound 1,3-dicyclohexylcarbodiimide (0.4 g, 0.6 mmol, 1.52 mmol/g) in a 1:1 mixture of dichloromethane and DMF (4 ml) was stirred at room temperature for 30 min. A solution of 1-(2-methoxy-ethyl)-piperidine-4-carboxylic acid hydrochloride [WO 97/25309] (0.098 g, 0.44 mmol) in DMF (2 ml) was then added and the mixture stirred at room temperature overnight. The reaction mixture was then filtered, the solvent removed in vacuo and the crude residue purified by silica gel chromatography eluting with a 1:9:90 mixture of 0.88 ammonia solution:methanol:dichloromethane to give the title compound (0.12 g, 80%) as a yellow oil; MS(AP+) m/e 516 [M+H]$^+$.

Step 2: 1-(2-Methoxy-ethyl)-piperidine-4-carboxylic acid {2-[5-(1-hydroxyimino-indan-5-yl)-4-pyridin-4-yl-1H-imidazol-2-yl]-2-methyl-propyl}-amide The title compound (0.07 g, 70%) was prepared from the product of Step 1 as described in Example 1 Step 7; MS(AP+) m/e 531 [M+H]$^+$.

EXAMPLE 4

5-(2-Piperidin-4-yl-5-pyridin-4-yl-1H-imidazol-4-yl)-indan-1-one oxime

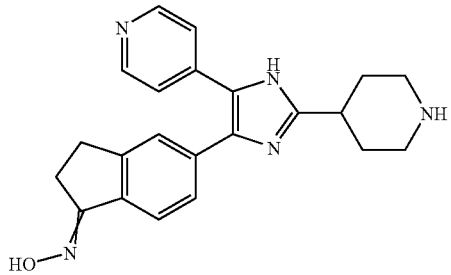

Step 1. 4-[4-(1-Methoxyimino-indan-5-yl)-5-pyridin-4-yl-1H-imidazol-2-yl]-piperidine-1-carboxylic acid tert-butyl ester The title compound (0.765 g, 79%) was prepared from the product of Example 1 Step 4 and 4-formyl-piperidine-1-carboxylic acid tert-butyl ester (S. I. Klein et al; *J. Med. Chem.*, 1998, 41, 2492) as described in Example 1 Step 5; MS(AP+) m/e 488 [M+H]$^+$.

Step 2. 5-(2-Piperidin-4-yl-5-pyridin-4-yl-1H-imidazol-4-yl)-indan-1-one

The title compound (0.55 g, 90%) was prepared from the product of Step 1 as described in Example 1 Step 6; MS(AP+) m/e 359 [M+H]$^+$.

Step 3. 5-(2-Piperidin-4-yl-5-pyridin-4-yl-1H-imidazol-4-yl)-indan-1-one oxime

The title compound (0.35 g, 90%) was prepared from the product of Step 2 as described in Example 1 Step 7 followed by purification by silica gel chromatography eluting with 0.88 ammonia solution: methanol: dichloromethane mixtures. MS(AP+) m/e 374 [M+H]$^+$.

EXAMPLE 5

5-[2-(1-{1-[1-(2-Methoxy-ethyl)-piperidin-4-yl]-mathanoyl}-piperidin-4-yl)-5-pyridin-4-yl-1H-imidazol-4-yl]-indan-1-one oxime

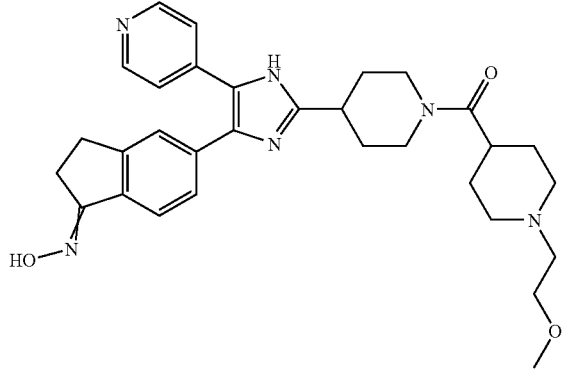

The title compound (0.028 g, 28%) was prepared from the product of Example 4 and 1-(2-methoxy-ethyl)-piperidine-4-carboxylic acid hydrochloride [WO 97/25309] as described in Example 3 Step 1; MS(AP+) m/e 543 [M+H]⁺.

EXAMPLE 6

5-[2-(1-Furan-3-ylmethyl-pipieridin-4-yl)-5-pyridin-4-yl-1H-imidazol-4-yl]-indan-1-one oxime

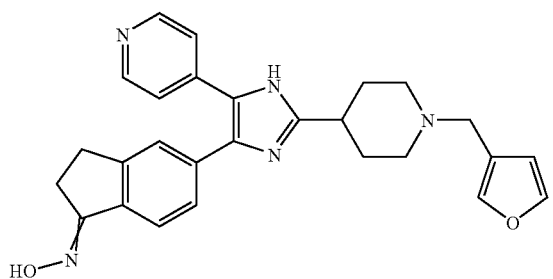

A mixture of the product of Example 4 (0.093 g, 0.25 mmol), 3-furaldehyde (0.024 g, 0.25 mmol) and polymer bound trimethylammonium cyanoborohydride (0.125 g, 0.5 mmol, 4 mmol/g) in methanol (3 ml) containing acetic acid (0.1 ml) was stirred at room temperature for 24 hours. The reaction mixture was poured onto the top of an SCX column eluting with 0.880 ammonia solution: methanol mixtures (0–10%), the product was then purified further by silica gel chromatography eluting with a 1:9:90 mixture of 0.880 ammonia solution: ethanol: dichloromethane to give the title compound (0.070 g, 62%) as a solid; MS(AP+) m/e 454 [M+H]⁺.

EXAMPLE 7

5-{2-[1-(2-Methoxy-ethyl)-piperidin-4-yl]-5-pyridin-4-yl-1H-imidazol-4-yl}-indan-1-one oxime

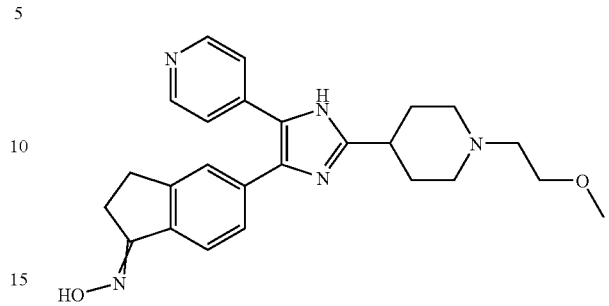

Step 1. 1-(2-Methoxy-ethyl)-piperidine-4-carbaldehyde

To a solution of 1-(2-methoxy-ethyl)-piperidine-4-carboxylic acid ethyl ester [WO97/25309] (2.0 g, 9.3 mmol) in toluene (40 ml) at −78° C. was added diisobutylaluminum hydride (10.2 ml, 1M solution in tetrahydrofuran, 10.2 mmol) over 1 hour. After 1 hour the reaction mixture was quenched with methanol (5 ml) and saturated ammonium acetate solution (5 ml). The mixture was stirred at room temperature for 1 hour and then filtered. The filtrate was concentrated to give the title compound as a yellow oil (1.1 g, 69%); MS(AP+) m/e 172 [M+H]⁺.

Step 2. 5-{2-[1-(2-Methoxy-ethyl)-piperidin-4-yl]-5-pyridin-4-yl-1H-imidazol-4yl}-indan-1-one O-methyl-oxime The title compound (0.27 g, 32%) was prepared from the product of Step 1 and the product of Example 1 Step 4 as described in Example 1 Step 5; MS(AP+) m/e 446 [M+H]⁺.

Step 3. 5-{2-[1-(2-Methoxy-ethyl)-piperidin-4-yl]-5-pyridin-4-yl-1H-imidazol-4-yl}-indan-1-one The title compound (0.193 g, 93%) was prepared from the product of Step 2 as described in Example 1 Step 6; MS(AP+) m/e 417 [M+H]⁺.

Step 4. 5-{2-[1-(2-Methoxy-ethyl)-piperidin-4-yl]-5-pyridin-4-yl-1H-imidazol-4-yl}-indan-1-one oxime The title compound (0.105 g, 68%) was prepared from the product of Step 3 as described in Example 4 Step 3; MS(AP+) m/e 432 [M+H]⁺.

EXAMPLE 8

5-(2-Aminomethyl-5-pyridin-4-yl-1H-imidazol-4-yl)-indan-1-one oxime

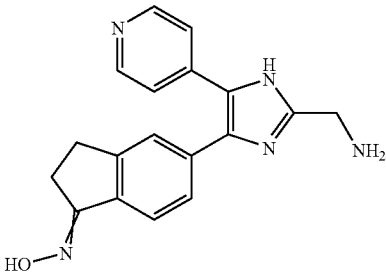

Step 1. [4-(1-Methoxyimio-indan-5-yl)-5-pyridin-4-yl-1H-imidazol-2-ylmethyl]-carbamic acid tert-butyl ester The title compound (1.04 g, 70%) was prepared from the product of Example 1 Step 4 and (2-oxo-ethyl)-carbamic acid tert-butyl ester as described in Example 1 Step 5; MS(AP+) m/e 434 [M+H]⁺.

Step 2. 5-(2-Aminomethyl-5-pyridin-4-yl-1H-imidazol-4-yl)-indan-1-one

The title compound (0.21 g, 30%) was prepared from the product of Step 1 as described in Example 1 Step 6; MS(AP+) m/e 305 [M+H]+.

Step 3. 5-(2-Aminomethyl-5-pyridin-4-yl-1H-imidazol-4-yl)-indan-1-one oxime

The title compound (0.064 g, 80%) was prepared from the product of Step 2 as described in Example 4 Step 3; MS(AP+) m/e 320 [M+H]+.

EXAMPLE 9

1-(2-Methoxy-ethyl)-piperidine-4-carboxylic acid [4-(1-hydroxyimino-indan-5-yl)-5-pyridin-4-yl)-1H-imidazol-2-ylmethyl]-amide

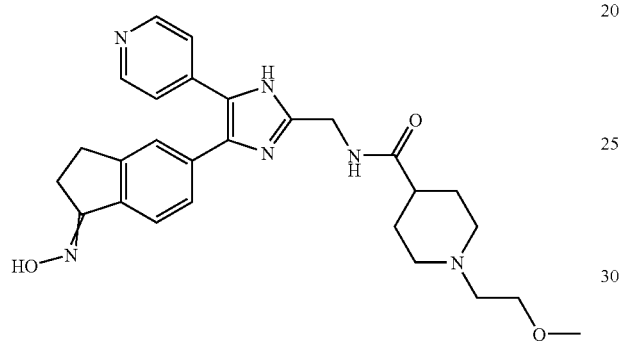

Step 1. 1-(2-Methoxy-ethyl)-piperidine-4-carboxylic acid [4(1-oxo-indan-5-yl)-5-pyridin-4-yl)-1H-imidazol-2-ylmethyl]-amide The title compound (0.095 g, 67%) was prepared from the product of Example 8 Step 2 and 1-(2-methoxy-ethyl)-piperidine-4-carboxylic acid hydrochloride [WO 97/25309] as described in Example 3 Step 1; MS(AP+) m/e 474 [M+H]+.

Step 2. 1-(2-Methoxy-ethyl)-piperidine-4-carboxylic acid [4-(1-hydroxyimino-indan-5-yl)-5-pyridin-4-yl)-1H-imidazol-2-ylmethyl]-amide The title compound (0.041 g, 42%) was prepared from the product of Step 1 as described in Example 4 Step 3; MS(AP+) m/e 531[M+H]+.

EXAMPLE 10

5-(2-Piperidin-1-ylmethyl-5-pyridin-4-yl-1H-imidazol-4-yl)-indan-1-one oxime

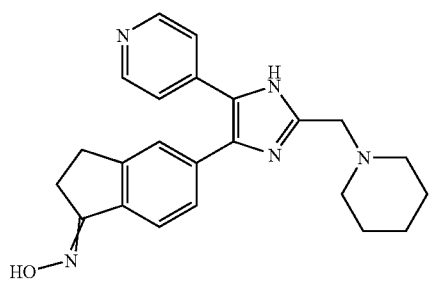

Step 1. 5-[2-(1,1-Dimethoxy-methyl)-5-pyridin-4-yl-1H-imidazol-4-yl]-indan-1-one O-methyl oxime.

The title compound (1.05 g, 79%) was prepared from the product of Example 1 Step 4 and dimethoxy-acetaldehyde (45% solution in tert-butyl methyl ether) as described in Example 1 Step 5; MS(AP+) m/e 379 [M+H]+.

Step 2. 4-(1-oxo-indan-5-yl)-5-pyridin-4-yl-1H-imidazole-2-carbaldehyde

The title compound (0.92 g, 90%) was prepared from the product of Step 1 as described in Example 1 Step 6; MS(AP+) m/e 303 [M+H]+.

Step 3. 5-(2-Piperidin-1-ylmethyl-5-pyridin-4-yl-1H-imidazol-4-yl)-indan-1-one.

The title compound (0.11 g, 44%) was prepared from the product of Step 2 and piperidine as described in Example 6; MS(AP+) m/e 373 [M+H]+.

Step 4. 5-(2-Piperidin-1-ylmethyl-5-pyridin-4-yl-1H-imidazol-4-yl)-indan-1-one oxime.

The title compound (0.55 g, 53%) was prepared from the product of Step 3 as described in Example 4 Step 3; MS(AP+) m/e 387 [M+H]+.

EXAMPLE 11

5-(2-morpholin-4-ylmethyl-5-pyridin-4-yl-1H-imidazol-4-yl)-indan-1-one oxime

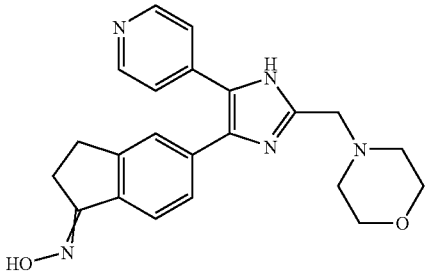

The title compound (0.034 g, 13%) was prepared from the product of Example 10 Step 2 and morpholine according to the procedures described in Example 10 Steps 3 and 4; MS(AP+) m/e 390 [M+H]+.

EXAMPLE 12

5-(5-Pyridin-4-yl-2-(2,3,5,6-tetrahydro-[1,2']bipyrazin-4-ylmethyl)-1H-imidazol-4-yl]-indan-1-one oxime

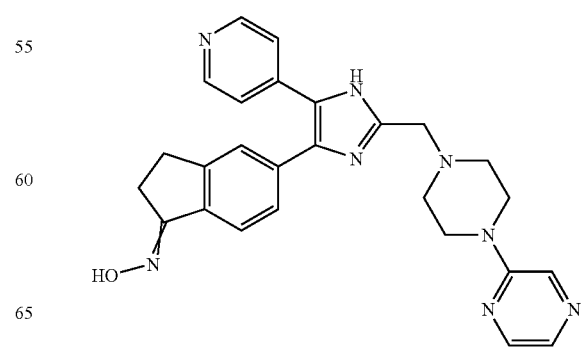

The title compound (0.038 g, 17%) was prepared from the product of Example 10 Step 2 and 3,4,5,6-tetrahydro-2H-[1,2']bipyrazinyl according to the procedures described in Example 10 Steps 3 and 4; MS(AP+) m/e 467 [M+H]+.

EXAMPLE 13

5-(2-Piperazin-1-ylmethyl-5-pyridin-4-yl-1H-imidazol-4-yl]-indan-1-one oxime

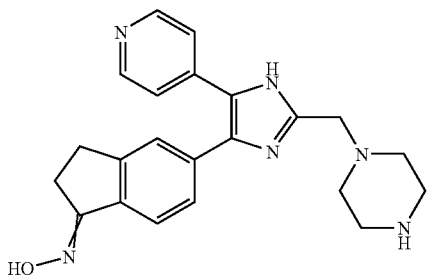

Step 1. 4-[4-(1-Oxo-indan-5-yl)-5-pyridin-4-yl-1H-imidazol-2-methyl]piperazine-1-carboxylic acid tert-butyl ester.

The title compound (0.35 g, 74%) was prepared from the product of Example 10 Step 2 and piperazine-1-carboxylic acid tert-butyl ester as described in Example 6; MS(AP+) m/e 474 [M+H]+.

Step 2. 5-(2-Piperazin-1-ylmethyl-5-pyridin-4-yl-1H-imidazol-4-yl)-indan-1-one.

A solution of the product of Step 1 (0.350 g, 0.74 mmol) in dichloromethane (10 ml) and trifluoroacetic acid (5 ml) was stirred at room temperature for 3 hours. The solution was concentrated and the residue co-evaporated with dichloromethane. The residue was dissolved in water (10 ml) and the solution was neutralised with sodium carbonate solution. The solvent was evaporated in vacuo and the resulting solid was dried over phosphorus pentoxide to give title compound which was used in the next step; MS(AP+) m/e 374 [M+H]+.

Step 3. 5-(2-Piperazin-1-ylmethyl-5-pyridin-4-yl-1H-imidazol-4-yl]-indan-1-one oxime.

The title compound (0.105 g, 37%) was prepared from the product of Step 2 as described in Example 4 Step 3; MS(AP+) m/e 389 [M+H]+.

Example 14

5-{2-[4-(3-Dimethylamino-propyloxy)-phenyl]-5-pyridin-4-yl-1H-imidazol-4-yl}-indan-1-one

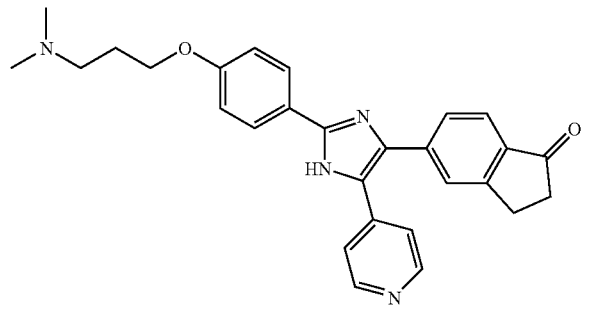

Step 1: 5-Bromo-indan-1-one O-methyl-oxime

To a solution of 5-bromo-indanone (100 g, 0.474 mol) in ethanol (650 ml) under argon was added methoxylamine hydrochloride (198 g, 2.38 mol) and pyridine (125 ml). The mixture was refluxed for 2.5 hours, cooled to room temperature and poured into saturated aqueous sodium hydrogen carbonate solution. The mixture was then extracted with ethyl acetate and the organic phase dried (sodium sulphate) and then concentrated in vacuo. The crude material was recrystallised from isopropanol to furnish the title compound, (110 g, 97%), as a brown solid; $^1$HMR (CDCl$_3$) 7.52 (1H, d, J 8.3 Hz), 7.43 (1H, d, J 1 Hz), 7.35 (1H, dd, J 8.3, 1Hz), 3.97 (3H, s), 2.99 (2H, m), 2.99 (2H, m), 2.85 (2H, m).

Step 2: 1-Methoxyimino-indan-5-carbaldehyde

To a solution of the product of Step 1 (112 g, 0.46 mol) in THF (1500 ml) at −60° C. under argon, was added n-BuLi (325 ml, 0.52 mol) over 1 hour. After stirring at −60° C. for 1 hour a solution of DMF (39.7 ml) in THF (50 ml) was added dropwise over 1 hour. The reaction was stirred at −60° C. for 1 hour before being allowed to warm to room temperature. After 1 hour the reaction was quenched with saturated aqueous sodium hydrogen carbonate solution and extracted into ethyl acetate. The organic phase was then dried (sodium sulphate), concentrated in vacuo and the residue purified by silica gel chromatography, to give the title compound (57 g, 65%) as a yellow solid; $^1$H NMR (CDCl$_3$) 10.0 (1H, s), 7.83–7.73 (3H, m), 4.02 (3H, s), 3.10 (2H, m), 2.92 (2H, m).

Step 3: 5-(1,2-Dihydroxy-2-pyridin-4-yl-ethyl)-indan-1-one-O-methyl-oxime

To a solution of 4-(tert-butyl-dimethyl-silanyloxymethyl)-pyridine [T. F. Gallagher et al; Bioorg. Med. Chem., 1997, 5, 49] (71.5 g, 0.32 mol) in THF (800 ml) at −50° C. under argon was added LDA (162 ml, 2M in heptane/THF/ethylbenzene, 0.324 mol) over 1 hour. The mixture was stirred at −40° C. for a further 1 hour before a solution of the product of Step 2 (55 g, 0.29 mol) in THF (600 ml) was added over 1 hour. The reaction was then allowed to warm to room temperature overnight before being quenched by the addition of saturated aqueous sodium hydrogen carbonate solution and then extracted into ethyl acetate. The organic phase was dried (sodium sulphate) and concentrated in vacuo to give a brown oil (125 g).

The oil was then dissolved in THF (1500 ml), treated with TBAF (356 ml, 0.356 mol) and stirred for 1 hour. The reaction mixture was then evaporated and the residue partitioned between water and ethyl acetate. The organic phase was then dried (sodium sulphate) and concentrated to give the title compound (57 g, 64%) as a pale yellow solid which was used without further purification. $^1$H NMR (CDCl$_3$) 8.38 (2H, m), 7.57 (1H, m), 7.12–6.99 (4H, m), 4.88 (1H, m), 4.66 (1H, m), 3.96 (3H, s), 2.93 (2H, m), 2.85 (2H, m).

Step 4: 1-(1-Methoxyimino-indan-5-yl)-2-pyridin-4-yl-ethane-1,2-dione

To a mixture of DMSO (43 ml, 0.56 mol) and dichloromethane (800 ml) at −70° C. under argon, was added oxalyl chloride (43.2 g) and then a solution of the product of Step 3 (55 g, 0.185 mol) in a mixture of dichloromethane/DMSO (1000 ml/60 ml) over 2 hours at −60° C. After stirring for 2 hours at −60° C., triethylamine (154 ml) was added dropwise and the mixture then allowed to warm to room temperature overnight. The reaction mixture was then quenched with water, the organic phase separated then washed with water, dried (sodium sulphate) and concentrated to yield the title compound (51 g, 94%) as a yellow solid. $^1$H NMR (CDCl$_3$) 8.87 (2H, d), 7.89–7.77 (5H, m), 4.03 (3H, s), 3.09 (2H, m), 2.93 (2H, m).

Step 5: 5-{2-[4(3-Dimethylamino-propyloxy)-phenyl]-5-phenyl-1H-imidazol-4-yl}-indan-1-one O-methyl-oxime A mixture of the product of Step 4 (0.3 g, 1.02 mmol), 4-(3-dimethylamino-propyloxy)-benzaldehyde (0.27 ml, 1.33 mmol) and ammonium acetate (0.785 g, 10.2 mmol) in acetic acid (10 ml) was heated to 100° C. for 1 hour. The reaction was then cooled to room temperature, poured into ice/0.880 ammonia solution and extracted with ethyl acetate. The organic extract was then dried (magnesium sulphate), concentrated in vacuo and the crude material purified by silica gel chromatography eluting with a 1:9:90 mixture of 0.88 ammonia solution:methanol:ethyl acetate to give the title compound (0.08 g, 16%) as a yellow solid; MS(AP+) m/e 483 [M+H]$^+$.

Step 6: 5-{2-[4(3-Dimethylamino-propyloxy)-phenyl]-5-pyridin-4-yl-1H-imidazol-4-yl}-indan-1-one A mixture of the product of Step 5 (0.07 g, 0.146 mmol) and 5M HCl (4 ml) in dioxan (3 ml) was heated to 100° C. for 1 hour. Acetone (3 ml) was then added and the heating continued for a further 1.5 hours before the mixture was cooled to room temperature, neutralised with 1M sodium hydroxide solution and extracted with ethyl acetate. The organic extract was then washed with water, dried (magnesium sulphate), concentrated in vacuo and the crude material purified by silica gel chromatography, eluting with a 2:18:80 mixture of 0.88 ammoniasolution:methanol:ethyl acetate to give the title compound (0.035 g, 53%) as a yellow solid; MS(AP+) m/e 453 [M+H]$^+$.

EXAMPLE 15

5-{2-[4-(3-Dimethylamino-propyloxy)-phenyl]-5-pyridin-4-yl-1H-imidazol-4-yl}-indan-1-one oxime

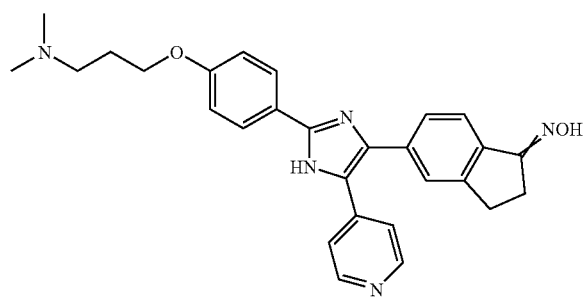

Step 1: 5-{2-[4(3-Dimethylamino-propyloxy)-phenyl]-5-pyridin-4-yl-1H-imidazol-4-yl}-indan-1-one oxime To a solution of the product of Example 14, Step 6 (0.07 g, 0.155 mmol) in ethanol (3 ml) at 80° C. was added aqueous hydroxylamine (1.5 ml, 50% in water). After 30 minutes the mixture was cooled to room temperature and concentrated in vacuo to give the title compound, (0.072 g, 100%) as a yellow solid; MS(AP+) m/e 468 [M+H]$^+$.

EXAMPLE 16

5-{2-[4(2-Dimethylamino-ethoxy)-phenyl]-5-pyridin-4-yl-1H-imidazol-4-yl}-1-indanone

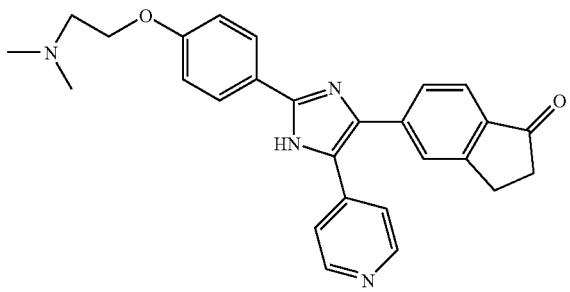

Step 1: 5-{2-[4-(2-Dimethylamino-ethoxy)-phenyl]-5-pyridin-4-yl-4H-imidazol-4-yl}-indan-1-one-O-methyl-oxime The title compound (0.19 g, 30%) was prepared from the product of Example 14 Step 4 and 4-(2-dimethylamino-ethoxy)-benzaldehyde [WO 99/19293] as described in Example 14 Step 5; MS(AP+) m/e 468 [+H]$^+$.

Step 2: 5-{2-[4-(2-Dimethylamino-ethoxy)-phenyl]-5-pyridin-4-yl-1H-imidazol-4-yl}-1-indanone The title compound (0.313 g, 56%) was prepared from the product of Step 1 as described in Example 14 Step 6; MS(AP+) m/e 439 [M+H]$^+$.

EXAMPLE 17

5-{2-[4-(2-Dimethylamino-ethoxy)-phenyl]-5-pyridin-4-yl-1H-imidazol-4-yl}-indan-1-one oxime

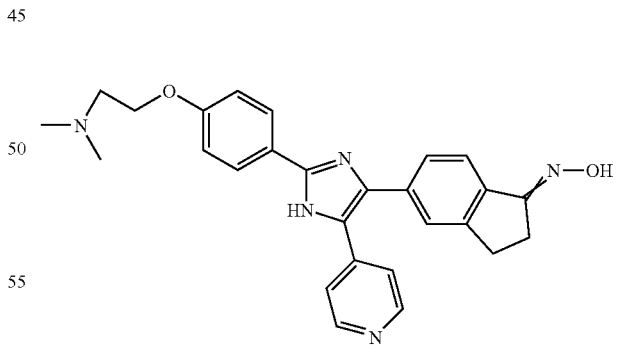

Step 1 5-{2-[4-(2-Dimethylamino-ethoxy)-phenyl]-5-pyridin-4-yl-1H-imidazol-4-yl}-indan-1-one oxime The title compound (0.321 g, 100%) was prepared from the product of Example 16 Step 2 as described in Example 15 Step 1; MS(AP+) m/e 454 [M+H]$^+$.

EXAMPLE 18

5-{2-[4-(2-Morpholin-4-yl-ethoxy)-phenyl]-5-pyridin 4-yl-1H-imidazol-4-yl}-indan-1-one

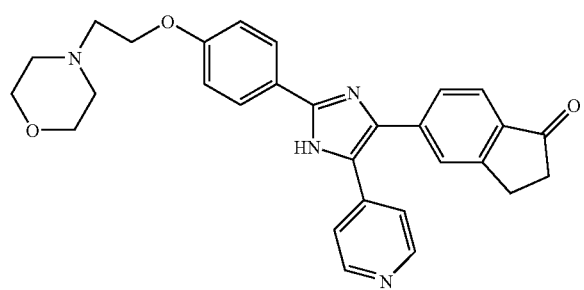

Step 1: 5-{2-[4-(2-Morpholin-4-yl-ethoxy)-phenyl]-5-pyridin-4-yl-1H-imidazol-4-yl}-indan-1-one-O-methyl-oxime The title compound (0.15 g, 20%) was prepared from the product of Example 14 Step 4 and 4-(2-morpholin-4-yl-ethoxy)-benzaldehyde [WO 96/28448] as described in Example 14 Step 5; MS(AP+) m/e 510 [M+H]$^+$ Step2: 5-{2-[4-(2-Morpholin-4-yl-ethoxy)-phenyl]-5-pyridin-4-yl-1H-imidazol-4-yl}-indan-1-one The title compound (0.048 g, 36%) was prepared from the product of Step 1 as described in Example 14 Step 6; MS(AP+) m/e 481 [M+H]$^+$.

EXAMPLE 19

5-{2-[4-(2-Morpholin-4-yl-ethoxy)-phenyl]-5-pyridin-4-yl-1H-imidazol-4-yl}-indan-1-one oxime

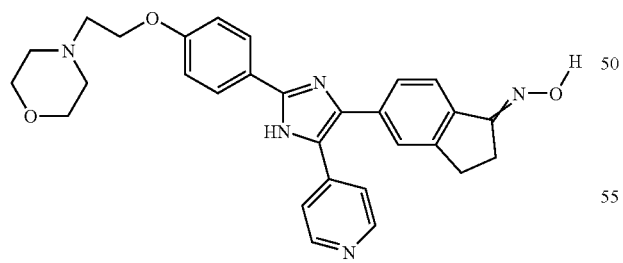

Step 1: 5-{2-[4-(2-Morpholin-4-yl-ethoxy)-phenyl]-5-pyridin-4-yl-1H-imidazol-4-yl}-indan-1-one oxime The title compound (0.048 g, 97%) was prepared from the product of Example 18 Step 2 as described in Example 15 Step 1; MS(AP+) m/e 496 [M+H]$^+$.

EXAMPLE 20

5-(5-Pyridin-4-yl-2-pyridin-3-yl-1H-imidazol-4-yl)-indan-1-one

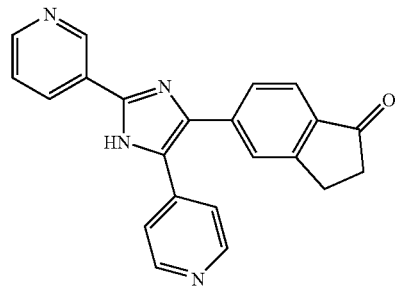

Step 1: 5-(5-Pyridin-4-yl-2-pyridin-3-yl-1H-imidazol-4-yl)-indan-1-one-O-methyl-oxime The title compound (0.11 g, 28%) was prepared from the product of Example 14 Step 4 and pyridine-3-carbaldehyde as described in Example 14 Step 5; MS(AP+) m/e 382 [M+H]$^+$.

Step 2: 5-(5-Pyridin-4-yl-2-pyridin-3-yl-1H-imidazol-4-yl)-indan-1-one

The title compound (0.025 g, 25%) was prepared from the product of Step 1 as described in Example 14 Step 6; MS(AP+) m/e 353 [M+H]$^+$.

EXAMPLE 21

5-(5-Pyridin-4-yl-2-pyridin-3-yl-1H-imdazol-4-yl}-indan-1-one oxime

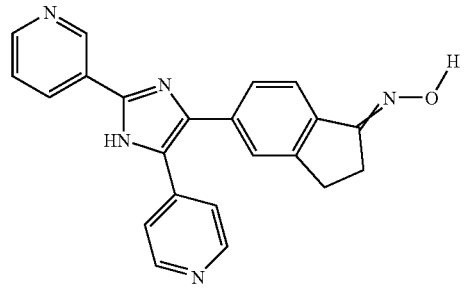

Step 1: 5-(5-Pyridin-4-yl-2-pyridin-3-yl-1H-imidazol-4-yl}-indan-1-one oxime

The title compound (0.075 g, 76%) was prepared from the product of Example 20 Step 2 as described in Example 15 Step 1; MS(AP+) m/e 368[M+H]$^+$.

EXAMPLE 22

5-(2-Phenyl-5-pyridin-4-yl-1H-imidazol-4-yl)-indan-1-one

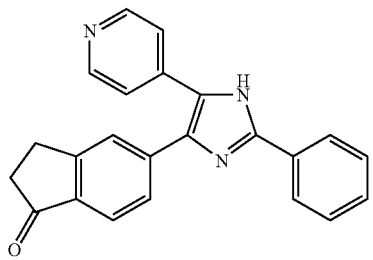

Step 1: 4-[2-Phenyl-1-(2-trimethylsilanyl-ethoxymethyl)-1H-imidazol-4-yl]-pyridine 4-(2-Phenyl-1H-imidazol-4-yl)-pyridine [N. J. Liverton et. al., *J. Med. Chem.*, 1999, 42, 2180] (17.8 g, 80.5 mmol) was dissolved in DMF (150 ml) and cooled to 0° C. The solution was then treated with sodium hydride (3.54 g, 60% dispersion, 88.6 mmol), and stirred for 25 minutes maintaining the temperature of 0° C.

2-(Trimethylsilyl)ethoxymethyl chloride (14.77 g, 88.6 mmol) was then added dropwise over 5 minutes and the mixture warmed to room temperature overnight. The reaction was then poured into a saturated solution of sodium hydrogen carbonate and extracted several times with diethyl ether. The combined ether extracts were then dried (sodium sulphate), concentrated in vacuo and the residue purified by silica gel chromatography, eluting with ethyl acetate to give the title compound as a pale yellow solid (16.8 g, 59%); MS(AP+) m/e 353 [M+H]+.

Step 2: 4-[5-Bromo-2-phenyl-1-(2-trimethylsilanyl-ethoxymethyl)-1H-imidazol-4-yl]-pyridine To a solution of the product of Step 1 (15 g, 42.6 mmol) in dichloromethane (300 ml) at room temperature was added bromine (6.81 g, 2.38 ml, 46.5 mmol) followed by a saturated solution of sodium carbonate (150 ml). The mixture was stirred for 40 minutes before being separated and the organic layer washed successively with water and brine. The organic layer was then dried (magnesium sulphate) and concentrated in vacuo to give the title compound (18.1 g, 99%) as a brown viscous oil which was used without further purification; MS(AP+) m/e 431/433 [M+H]+.

Step 3: 4-[2-Phenyl-5-tributylstannanyl-1-(2-trimethylsilanyl-ethoxymethyl)-1H-imidazol-4-yl]-pyridine.

To a solution of the product of Step 2 (13.4 g, 31.2 mmol) in THF (200 ml) at −78° C. was added dropwise $^t$BuLi (22 ml, 1.7M, 38 mmol). After 25 minutes tributyltin chloride (12.37 g, 10.3 ml, 38 mmol) was added dropwise and the mixture was then allowed to reach room temperature overnight. The reaction was then poured into a saturated solution of sodium hydrogen carbonate and washed several times with diethyl ether. The combined organic layers were dried (magnesium sulphate), concentrated in vacuo and the residue purified by silica gel chromatography, eluting with a 0.5:4.5:45:50 mixture of 0.88 ammonia solution:methanol:hexane:diethyl ether to give the title compound (18.5 g, 93%) as a brown viscous oil; MS(AP+) m/e 641/643/644 [M+H]+.

Step 4: 5-[2-Phenyl-5-pyridin-4-yl-3-(2-trimethylsilanyl-ethoxymethyl)-1H-imidazol-4-yl]-indan-1-one Palladium acetate (0.025 g, 0.11 mmol) and triphenylphosphine (0.06 g, 0.22 mmol) were suspended in toluene (1 ml). 5-bromoindanone (240 mg, 1.1 mmol) was then added and the mixture heated to 100° C. for 5 min. The solution was then treated with a solution of the product of Step 3 (0.6 g, 0.94 mmol) in toluene (1 ml) and stirred for 18 hours at 100° C. After cooling the solvent was removed in vacuo and the residue purified by silica gel chromatography, eluting with ethyl acetate to afford the title compound (0.25 g, 55%) as a yellow solid; MS(AP+) m/e 482 [M+H]+.

Step 5: 5-(2-Phenyl-5-pyridin-4-yl-1H-imidazol-4-yl)-indan-1-one

The product of Step 4 (0.32 g, 0.66 mmol) was dissolved in ethanol (4 ml), 5M aqueous hydrochloric acid solution (3 ml) added and the mixture heated to reflux for 30 min. On cooling, the solvent was removed in vacuo to afford the title compound as a yellow solid (0.27 g, 96%); MS(AP+) m/e 352 [M+H]+.

EXAMPLE 23

5-(2-Phenyl-5-pyridin-4-yl-1H-imidazol-4-yl)-indan-1-one oxime

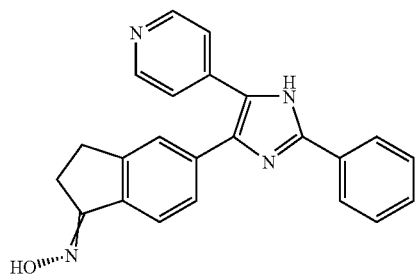

Step 1: 5-(2-Phenyl-5-pyridin-4-yl-1H-imidazol-4-yl)-indan-1-one oxime

A solution of the product of Example 22 Step 5 (0.06 g, 0.17 mmol) and hydroxylamine hydrochloride (0.035 g, 0.5 mmol) in 40% aqueous sodium hydroxide (2 ml) and ethanol (3 ml) was heated to reflux for 30 min. On cooling the mixture was neutralised with aqueous 2M hydrochloric acid and extracted into ethyl acetate. The organic layer was washed with brine, dried (magnesium sulphate) and concentrated in vacuo. The residue was purified by silica gel chromatography eluting with a 1:9:90 mixture of 0.88 ammonia solution: methanol: dichloromethane to give the title compound (0.05 g, 80%) as a yellow solid; MS(AP+) m/e 367 [M+H]+.

BIOLOGICAL EXAMPLES

The activity of compounds of formula (I) as B-Raf inhibitors may be determined by the following in vitro assays:

Fluorescence Anisotropy Kinase Binding Assay

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×$K_i$) of a potent inhibitor the anisotropy of the unbound fluorescent ligand is measurably different from the bound value.

The concentration of kinase enzyme should preferably be $\geq 1 \times K_f$. The concentration of fluorescent ligand required will depend on the instrumentation used, and the fluorescent and physicochemical properties. The concentration used must be lower than the concentration of kinase enzyme, and preferably less than half the kinase enzyme concentration. A typical protocol is:

All components dissolved in Buffer of composition 50 mM HEPES, pH 7.5, 1 mM CHAPS, 10 mM $MgCL_2$.

B-Raf Enzyme concentration: 1 nM
Fluorescent ligand concentration: 0.5 nM
Test compound concentration: 0.1 nM–100 uM Components incubated in 10 ul final volume in LJL HE 384 type B black microtitre plate until equilibrium reached (Over 3 h, up to 30 h)

Fluorescence anisotropy read in LJL Acquest.

Definitions:
$K_i$=dissociation constant for inhibitor binding
$K_f$=dissociation constant for fluorescent ligand binding
The fluorescent ligand is the following compound:

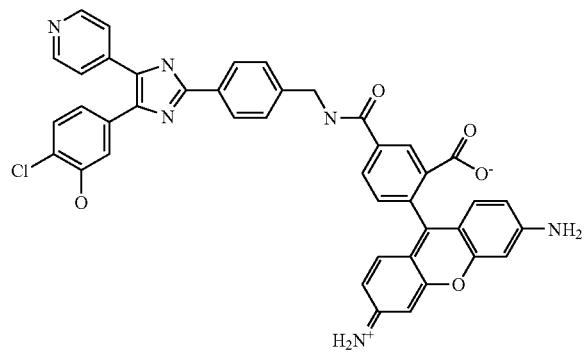

which is derived from 5-[2-(4-aminomethylphenyl)-5-pyridin-4-yl-1H-imidazol-4-yl]-2-chlorophenol and rhodamine green.

Raf Kinase Assay

Activity of human recombinant B-Raf protein was assessed in vitro by assay of the incorporation of radiolabelled phosphate to recombinant MAP kinase (MEK), a known physiologic substrate of B-Raf. Catalytically active human recombinant B-Raf protein was obtained by purification from sf9 insect cells infected with a human B-Raf recombinant baculovirus expression vector. To ensure that all substrate phosphorylation resulted from B-Raf activity, a catalytically inactive form of MEK was utilised. This protein was purified from bacterial cells expression mutant inactive MEK as a fusion protein with glutathione-S-transferase (GST-kdMEK).

Method: Standard assay conditions of B-Raf catalytic activity utilised 3 ug of GST-kdMEK, 10 uM ATP and 2 uCi $^{33}$P-ATP, 50 MM MOPS, 0.1 mM EDTA, 0.1M sucrose, 10 mM $MgCl_2$ plus 0.1% dimethylsulphoxide (containing compound where appropriate) in a total reaction volume of 30 ul. Reactions were incubated at 25° C. for 90 minutes and reactions terminated by addition of EDTA to a final concentration of 50 uM. 10 ul of reaction was spotted to P30 phosphocellulose paper and air dried. Following four washes in ice cold 10% trichloroacetic acid, 0.5% phosphoric acid, papers were air dried prior to addition of liquid scintillant and measurement of radioactvity in a scintillation counter.

Results: The compounds of the examples were found to be effective in inhibiting B-Raf mediated phosphorylation of GST-kdMEK substrate having $IC_{50}$'s of <3 μM.

The activity of compounds as Raf inhibitors may also be determined by the assays described in WO 99/10325; McDonald, O. B., Chen, W. J., Ellis, B., Hoffmnan, C., Overton, L., Rink, M., Smith, A., Marshall, C. J. and Wood, E. R (1999) A scintillation proximity assay for the Raf/MEK/ERK kinase cascade: high throughput screening and identification of selective enzyme inhibitors, Anal. Biochem. 268: 318–329 and AACR meeting New Orleans 1998 Poster 3793.

The neuroprotective properties of B-Raf inhibitors may be determined by the following in vitro assay:

Neuroprotective Properties of B-Raf Inhibitors in Rat Hippocampal Slice Cultures Organotypic cultures provide an intermediate between dissociated neuronal cell cultures and in-vivo models of oxygen and glucose deprivation (OGD). The majority of glial-neuronal interactions and neuronal circuitry are maintained in cultured hippocampal slices, so facilitating investigation of the patterns of death among differing cell types in a model that resembles the in vivo situation. These cultures allow the study of delayed cellular damage and death 24 hours, or more, post-insult and permit assessment of the consequences of long-term alterations in culture conditions. A number of laboratories have reported delayed neuronal damage in response to OGD in organotypic cultures of the hippocampus (Vornov et al., *Stroke*, 1994, 25, 57–465; Newell et al., *Brain Res.*, 1995, 676, 38–44). Several classes of compounds have been shown to protect in this model, including EAA antagonists (Strasser et al., *Brain Res.*, 1995, 687, 167–174), Na channel blockers (Tasker et al., *J. Neurosci.*, 1992, 12, 984–308) and Ca channel blockers (Pringle et al., *Stroke*, 1996, 7, 2124–2130). To date, relatively little is known of the roles of intracellular kinase mediated signalling pathways in neuronal cell death in this model.

Method: Organotypic hippocampal slice cultures were prepared using the method of Stoppini et al., *J. Neurosci. Methods*, 1995, 37, 173–182. Briefly, 400 micron sections prepared from hippocampi of 7–8 day postnatal Sprague Dawley rats are cultured on semiporous membranes for 9–12 days. OGD is then induced by incubation in serum and glucose-free medium in an anaerobic chamber for 45 minutes. Cultures are then returned to the air/$CO_2$ incubator for 23 hours before analysis. Propidium iodide (PI) is used as an indicator of cell death. PI is non toxic to neurones and has been used in many studies to ascertain cell viability. In damaged neurons PI enters and binds to nucleic acids. Bound PI shows increased emission at 635 nm when excited at 540 nm. One PI fluorescence image and one white light image are taken and the proportion of cell death analysed The area of region CA1 is defined from the white light image and superimposed over the PI image. The PI signal is thresholded and area of PI damage expressed as a percentage of the CA1 area. Correlation between PI fluorescence and histologically confirmed cell death has been validated previously by Niss1-staining using cresyl fast violet (Newell et al., *J. Neurosci.*, 1995, 15, 7702–7711).

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of composition, process, or use claims and may include by way of example and without limitation the following claims.

The invention claimed is:

1. A compound of formula (I):

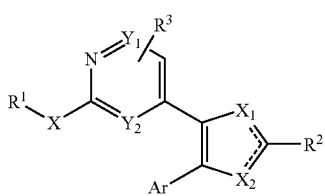

wherein

X is O, $CH_2$, CO, S or NH, or the moiety X—$R^1$ is hydrogen;

$Y_1$ and $Y_2$ are CH;

$R^1$ is hydrogen, $C_{1-6}$alkyl, $C_{3-7}$cycloalkyl, aryl, or aryl $C_{1-6}$alkyl, any of which may be optionally substituted; in addition, when X is $CH_2$ then $R^1$ may be hydroxy or $C_{1-6}$alkoxy which may be optionally substituted;

$R^2$ is H, $C_{1-6}$alkyl, $C_{2-6}$alkenyl, $C_{3-7}$cycloalkyl, $C_{5-7}$cycloalkenyl, or aryl, any of which may be optionally substituted;

Ar is a group of the formula a) or b):

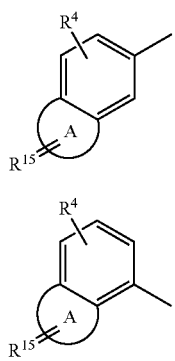

wherein A represents a fused 5-membered carbocyclic ring which ring is optionally substituted by up to 2 substituents selected from halogen, $C_{1-6}$alkyl, hydroxy, $C_{1-6}$alkoxy and keto;

$R^3$ and $R^4$ are independently selected from hydrogen, halogen, $C_{14}$alkyl, aryl, aryl $C_{1-6}$alkyl, $C_{1-6}$alkoxy, $C_{1-6}$alkoxy$C_{1-6}$alkyl, halo$C_{1-6}$alkyl, aryl$C_{1-6}$alkoxy, hydroxy, nitro, cyano, azido, amino, mono- and di-N-$C_{1-6}$alkylamino, acylamino, arylcarbonylamino, acyloxy, carboxy, carboxy salts, carbamoyl, mono- and di-N-$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkylsulphinyl and $C_{1-6}$alkylsulphonyl;

$R^{15}$ is O or N—OH;

one of $X_1$ and $X_2$ is N and the other is $NR^6$ wherein $R^6$ is hydrogen or $C_{1-6}$alkyl;

wherein the optional substituents for alkyl, alkoxy, alkenyl, cycloalkyl and cycloalkenyl groups are selected from aryl, $C_{1-6}$alkoxy, $C_{1-6}$alkylthio, aryl$C_{1-6}$alkoxy, aryl $C_{1-6}$alkylthio, amino, mono- or di-$C_{1-6}$alkylamino, aminosulphonyl, cycloalkyl, cycloalkenyl, carboxy, amide, ureido, guanidino, $C_{1-6}$alkylguanidino, amidino, $C_{1-6}$alkylamidino, $C_{1-6}$acyloxy, hydroxy, halogen, cyano and any combinations thereof;

wherein the aryl groups may be optionally substituted by a substituent selected from halogen, hydroxy, $C_{1-6}$alkyl, aryl, aryl$C_{1-6}$alkyl, $C_{1-6}$alkoxy, $C_{1-6}$alkoxy$C_{1-6}$alkyl, halo$C_{1-6}$alkyl, aryl$C_{1-6}$alkoxy, nitro, cyano, azido, amino, mono- and di-N-$C_{1-6}$alkylamino, acylamino, arylcarbonylamino, acyloxy, carboxy, carboxy salts, carbamoyl, mono- and di-N-$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, urea, carbamate, acyl, sulphonylamino, aminosulphonyl, $C_{1-6}$alkylthio, $C_{1-6}$alkylsulphinyl, $C_{1-6}$alkylsulphonyl, and any combination thereof;

or a pharmaceutically acceptable salt thereof.

2. A compound of formula (I) according to claim 1 wherein X is NH or X—$R^1$ is hydrogen.

3. A compound of formula (I) according to claim 1 wherein $R^{15}$ N—OH.

4. A compound of formula (I) according to claim 1 wherein $R^2$ is:
   i) —$CR^7R^8$—$CH_2$-Z, or —$CH_2$-Z wherein $R^7$ and $R^8$ independently represent hydrogen or optionally substituted $C_{1-6}$alkyl, or $R^7$ and $R^8$ together with the carbon atom to which they are attached form an optionally substituted $C_{3-7}$cycloalkyl or $C_{5-7}$cycloalkenyl ring; and Z is $NR^9R^{10}$, $NR^9C(Q)NR^9R^{10}$, $NR^9COOR^{10}$, $NR^9SO_2R^{10}$, or $NR^9C(Q)R^{10}$ wherein $R^9$ and $R^{10}$ are independently selected from hydrogen, $C_{1-6}$alkyl, $C_{3-7}$cycloalkyl, aryl, and aryl$C_{1-6}$alkyl, any of which may be optionally substituted; Q is O or S; or
   ii) optionally substituted phenyl.

5. A compound of formula (I) according to claim 1 wherein $R^3$ is hydrogen.

6. A compound of formula (I) according to claim 1 wherein $R^4$ is hydrogen.

7. A compound of formula (I) according to claim 1 wherein $R^6$ is hydrogen.

8. A compound of formula (I) according to claim 1, which is:

5-[2-(2-Amino-1,1-dimethyl-ethyl)-5-pyridin-4-yl-1H-imidazol-4-yl]-indan-1-one oxime;

N-{2-[5-(1-Hydroxyimino-indan-5-yl)-4-pyridin-4-yl-1H-imidazol-2-yl]-2-methyl-propyl}-methanesulfonamide;

5-(2-Aminomethyl-5-pyridin-4-yl-1H-imidazol-4-yl)-indan-1-one oxime;

5-{2-[4-(3-Dimethylamino-propyloxy)-phenyl]-5-pyridin-4-yl-1H-imidazol-4-yl}-indan-1-one;

5-{2-[4-(3-Dimethylamino-propyloxy)-phenyl]-5-pyridin-4-yl-1H-imidazol-4-yl}-indan-1-one oxime;

5-{2-[4-(2-Dimethylamino-ethoxy)-phenyl]-5-pyridin-4-yl-1H-imidazol-4-yl}-1-indanone;

5-{2-[4-(2-Dimethylamino-ethoxy)-phenyl]-5-pyridin-4-yl-1H-imidazol-4-yl}-indan-1-one oxime;

5-(2-Phenyl-5-pyridin-4-yl-1H-imidazol-4-yl)-indan-1-one;

5-(2-Phenyl-5-pyridin-4-yl-1H-imidazol-4-yl)-indan-1-one oxime, or a pharmaceutically acceptable salt thereof.

9. A pharmaceutical composition comprising the compound according to claim 1, or a pharmaceutically acceptable salt thereof, and a pharmaceutically acceptable carrier.

10. A pharmaceutical composition comprising the compound according to claim 8, or a pharmaceutically acceptable salt thereof, and a pharmaceutically acceptable carrier.

11. A method of therapeutic treatment of ischaemic stroke which method comprises administering to a human or other mammal a therapeutically effective amount of the compound according to claim 1 or a pharmaceutically acceptable salt thereof.

12. A method of therapeutic treatment of ischaemic stroke which method comprises administering to a human or other mammal a therapeutically effective amount of the compound according to claim 8 or a pharmaceutically acceptable salt thereof.

13. A compound of formula (I):

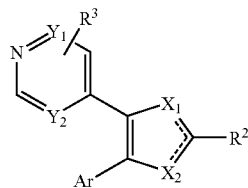

(I)

wherein
$Y_1$ and $Y_2$ are CH;
$R^2$ is optionally substituted phenyl, wherein the optional substituents are selected from halogen, hydroxy, $C_{1-6}$alkyl, aryl, aryl$C_{1-6}$-alkyl, $C_{1-6}$alkoxy, $C_{1-6}$alkoxy$C_{1-6}$alkyl, halo$C_{1-6}$alkyl, aryl$C_{1-6}$alkoxy, nitro, cyano, azido, amino, mono- and di-N-$C_{1-6}$alkylamino, acylamino, arylcarbonylamino, acyloxy, carboxy, carboxy salts, carbamoyl, mono- and di-N-$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, urea, carbamate, acyl, sulphonylamino, aminosulphonyl, $C_{1-6}$alkylthio, $C_6$alkylsulphinyl, $C_{1-6}$-alkylsulphonyl, and any combination thereof;
Ar is a group of the formula a) or b):

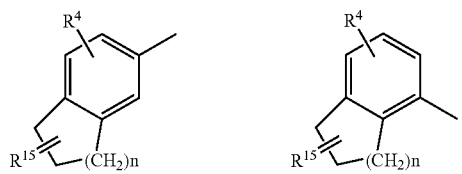

n is 1, $R^{15}$ is O or N—OH;
$R^3$ and $R^4$ are independently selected from hydrogen, halogen, $C_{1-6}$alkyl, aryl, aryl $C_{1-6}$alkyl, $C_{1-6}$alkoxy, $C_{1-6}$alkoxy$C_{1-6}$alkyl, halo$C_{1-6}$alkyl, aryl$C_{1-6}$alkoxy, hydroxy, nitro, cyano, azido, amino, mono- and di-N-$C_{1-6}$alkylamino, acylamino, arylcarbonylamino, acyloxy, carboxy, carboxy salts, carbamoyl, mono- and di-N-$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkylsulphinyl and $C_{1-6}$alkylsulphonyl;
one of $X_1$ and $X_2$ is N and the other is $NR^6$ wherein $R^6$ is hydrogen or $C_{1-6}$alkyl;
or a pharmaceutically acceptable salt thereof.

14. A compound of formula (I):

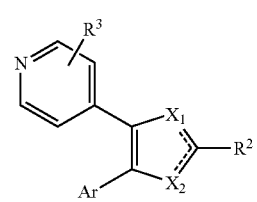

(I)

wherein
$R^2$ is phenyl, substituted by —O—$(CH_2)_m$—$NR^{18}R^{19}$ or —$(CH_2)_m$—$NR^{18}R^{19}$, wherein m is an integer from 1 to 6, and $R^{18}$ and $R^{19}$ independently represent hydrogen or $C_{1-6}$alkyl;
Ar is a group of the formula a) or b):

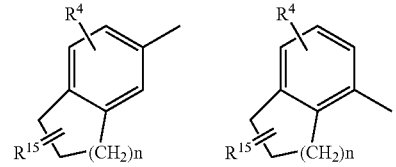

n is 1, $R^{15}$ is O or N—OH
$R^3$ are independently selected from hydrogen, halogen, $C_{1-6}$alkyl, aryl, aryl $C_{1-6}$alkyl, $C_{1-6}$alkoxy, $C_{1-6}$alkoxy$C_{1-6}$alkyl, halo$C_{1-6}$alkyl, aryl$C_{1-6}$alkoxy, hydroxy, nitro, cyano, azido, amino, mono- and di-N-$C_{1-6}$alkylamino, acylamino, arylcarbonylamino, acyloxy, carboxy, carboxy salts, carbamoyl, mono- and di-N-$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkylsulphinyl and $C_{1-6}$alkylsulphonyl;
one of $X_1$ and $X_2$ is N and the other is $NR^6$ wherein $R^6$ is hydrogen or $C_{1-6}$alkyl;
or a pharmaceutically acceptable salt thereof.

15. A compound according to claim 8, wherein said compounds is 5-{2-[4-(2-Dimethylamino-ethoxy)-phenyl]-5-pyridin-4-yl-1H-imidazol-4-yl}-indan-1-one oxime, or a pharmaceutically acceptable salt thereof.

16. A compound according to claim 15, wherein said compound is 5-{2-[4-(2-Dimethylamino-ethoxy)-phenyl]-5-pyridin-4-yl-1H-imidazol-4-yl}-indan-1-one oxime.

17. A pharmaceutical composition comprising the compound according to claim 16 or a pharmaceutically acceptable salt thereof, and a pharmaceutically acceptable carrier.

18. A pharmaceutical composition comprising the compound according to claim 16 and a pharmaceutically acceptable carrier.

19. A compound of formula (I) according to claim 4 wherein Q is O.

* * * * *